(12) United States Patent  
Addison et al.

(10) Patent No.: US 8,922,788 B2
(45) Date of Patent: Dec. 30, 2014

(54) METHODS AND SYSTEMS FOR DETERMINING A PROBE-OFF CONDITION IN A MEDICAL DEVICE

(71) Applicant: Covidien LP, Mansfield, MA (US)

(72) Inventors: Paul Stanley Addison, Edinburgh (GB); James Nicholas Watson, Dunfermline (GB)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/726,075

(22) Filed: Dec. 22, 2012

(65) Prior Publication Data

US 2014/0176944 A1    Jun. 26, 2014

(51) Int. Cl.
  *G01B 11/14*  (2006.01)
  *A61B 5/06*  (2006.01)
  *A61B 5/00*  (2006.01)
  *A61B 5/1455*  (2006.01)

(52) U.S. Cl.
  CPC ............... *G01B 11/14* (2013.01); *A61B 5/6822* (2013.01); *A61B 2562/0233* (2013.01); *A61B 5/6824* (2013.01); *A61B 5/6826* (2013.01); *A61B 5/7203* (2013.01); *A61B 5/4887* (2013.01); *A61B 5/1455* (2013.01); *A61B 5/6814* (2013.01); *A61B 5/061* (2013.01); *A61B 5/6829* (2013.01); *A61B 5/0059* (2013.01); *A61B 5/6815* (2013.01); *A61B 5/6844* (2013.01); *A61B 5/684* (2013.01)
  USPC .......................................... 356/614; 356/622

(58) Field of Classification Search
  USPC .......... 356/614–615, 620, 622; 600/310, 336, 600/324, 330–334, 481, 509, 544–547
  See application file for complete search history.

(56) References Cited

U.S. PATENT DOCUMENTS

| 4,621,643 A | 11/1986 | New, Jr. et al. |
| 5,503,148 A | 4/1996 | Pologe et al. |
| 5,846,190 A | 12/1998 | Woehrle |
| 5,924,985 A | 7/1999 | Jones |
| 5,934,277 A | 8/1999 | Mortz et al. |
| 6,360,114 B1 | 3/2002 | Diab |
| 6,398,727 B1 | 6/2002 | Bui et al. |
| 6,510,329 B2 | 1/2003 | Heckel |
| 6,526,300 B1 | 2/2003 | Kiani |
| 6,560,470 B1 | 5/2003 | Pologe |
| 6,600,940 B1 | 7/2003 | Fein et al. |
| 6,654,624 B2 | 11/2003 | Diab |
| 6,675,031 B1 | 1/2004 | Porges et al. |
| 6,771,994 B2 | 8/2004 | Kiani |

(Continued)

FOREIGN PATENT DOCUMENTS

| EP | 1792564 A1 | 6/2007 |
| WO | WO9843071 | 10/1998 |

OTHER PUBLICATIONS

International Search Report and Written Opinion of the International Searching Authority for application No. PCT/EP2013/077673, mailed on May 20, 2014.

*Primary Examiner* — Tri T Ton
(74) *Attorney, Agent, or Firm* — Shvarts & Leiz LLP

(57) ABSTRACT

A physiological monitoring system may determine a probe-off condition. A physiological sensor may be used to emit one or more wavelengths of light. A received light signal may be processed to obtain a light signal corresponding to the emitted light and an ambient signal. The signals may be analyzed to identify similar behavior. The system may determine whether the physiological sensor is properly positioned based on the analysis.

24 Claims, 10 Drawing Sheets

(56) References Cited

U.S. PATENT DOCUMENTS

| | | |
|---|---|---|
| 6,950,687 B2 | 9/2005 | Al-Ali |
| 6,985,762 B2 | 1/2006 | Brashears et al. |
| 6,987,994 B1 | 1/2006 | Mortz |
| 7,047,054 B2 | 5/2006 | Benni |
| 7,130,671 B2 | 10/2006 | Baker et al. |
| 7,313,427 B2 | 12/2007 | Benni |
| 7,457,652 B2 | 11/2008 | Porges et al. |
| 7,471,969 B2 | 12/2008 | Diab et al. |
| 2003/0139656 A1 | 7/2003 | Kiani et al. |
| 2004/0158134 A1 | 8/2004 | Diab |
| 2004/0158135 A1 | 8/2004 | Baker et al. |
| 2007/0208235 A1 | 9/2007 | Besson et al. |
| 2008/0039699 A1 | 2/2008 | Neumann |
| 2008/0221426 A1 | 9/2008 | Baker et al. |
| 2010/0094106 A1 | 4/2010 | Kiani |
| 2011/0237914 A1 | 9/2011 | Lamego et al. |
| 2011/0245622 A1 | 10/2011 | McKenna |
| 2012/0029310 A1 | 2/2012 | Paquet |

US 8,922,788 B2

METHODS AND SYSTEMS FOR DETERMINING A PROBE-OFF CONDITION IN A MEDICAL DEVICE

The present disclosure relates to determining a sensor condition, and more particularly relates to determining a probe-off condition in a pulse oximeter or other medical device.

SUMMARY

Methods and systems are provided for determining whether a physiological sensor is properly positioned on a subject. In some embodiments, a detected light signal may be received using the physiological sensor. The detected light signal may be processed to obtain a first signal corresponding to ambient light and a second signal corresponding to an emitted photonic signal and ambient light. The first and second signal may be analyzed to determine similar behavior, and it may be determined that the physiological sensor is not properly positioned based on the analysis.

In some embodiments, similar behaviors may include mimicking-equal behavior, mimicking-parallel behavior, nonlinear scaling, any other suitable behavior, or any combination thereof. For example, mimicking-equal or mimicking-parallel behavior may be identified when both the first and second signals move together or with a constant offset. In some embodiments, this behavior may be identified as a probe-off condition, and may be indicative of the same amount of light reaching the detector irrespective of light emitted by the system. In some embodiments, the system may identify a constant amplitude or signal flatness. A constant amplitude may be used alone or in combination with other signals to determine a probe-off condition.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
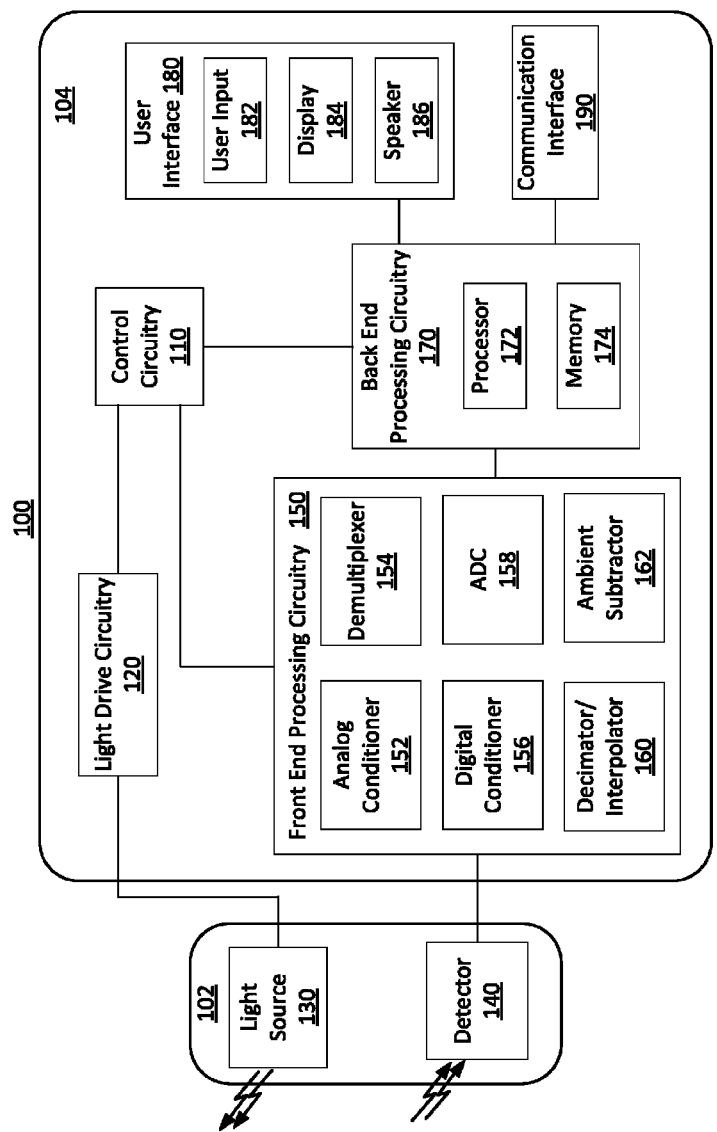
FIG. 1 is a block diagram of an illustrative physiological monitoring system in accordance with some embodiments of the present disclosure.

The present disclosure is directed towards determining a probe-off condition in a medical device. A physiological monitoring system may monitor one or more physiological parameters of a patient, typically using one or more physiological sensors. For example, the physiological monitoring system may include a pulse oximeter. The system may include, for example, a light source and a photosensitive detector. In some embodiments, a sensor may be attached to a target area of a patient. For example, the sensor may be attached using an adhesive, a strap, a band, elastic, any other suitable attachment, or any combination thereof. In some embodiments, the sensor may be located proximate to a desired structural element. For example, a sensor may be held near to the radial artery using a wrist strap. In another example, a sensor may be held near to the blood vessels of the forehead using an adhesive, tape, a headband strap, any other suitable attachment, or any combination thereof. In a further example, a sensor may be held near the blood vessels on a fingertip using an adhesive, tape or mechanical clip.

In some embodiments, the system may determine a probe-off condition. As used herein, the probe-off condition may include any condition where the sensor is fully or partially detached or moved from the desired target area of the subject. A probe-off condition may include a condition where an adhesive coupling the sensor to the subject has fully or partially failed. A probe-off condition may include a condition where a sensor held with a strap or band has loosened, shifted, slid, moved, detached, repositioned in any other unsuitable arrangement, or any combination thereof. For example, a sensor held by an adhesive to the forehead of a subject may fully or partially separate due to an adhesive failure, resulting in a probe-off condition. In another example, a sensor held proximal to the radial artery at the wrist of a subject by a strap or band may shift out of position, resulting in a probe-off position. It will be understood that the probe-off conditions described here are merely exemplary and that any suitable undesirable positioning of the sensor may result in a probe-off condition. It will also be understood that the particular arrangement of a probe-off condition may dependent upon the configuration and type of probe.

The probe-off condition may be detected by the system. In some embodiments, the system may use a detected ambient signal and a detected light signal to determine a probe-off condition. As used herein, the emitted photonic signal is a light signal emitted by the system. As used herein, a received light signal is a light signal received by a detector of the system. As used herein, a detected light signal is a light signal corresponding to light detected during the "on" period of a multiplexed drive. As used herein, a detected emitted light signal is a light signal corresponding to light from the emitted photonic signal. As used herein, a detected ambient light signal is a light signal corresponding to light detected during the "off" period of a multiplexed drive signal. In some embodiments, the received light signal is split into one or more detected light signals and one or more ambient light signals by demultiplexing. It will be understood that in some embodiments, the detected light signal may be the same or similar to the detected emitted light signal (e.g., when there is no ambient light or when the ambient light is filtered out prior to detection).

As will be described in detail below, a detected ambient signal may include information related to the amount of light a detector receives when one or more associated light sources are in an "off" state. Detected ambient signals may be time division multiplexed in a drive pulse modulation technique. In some embodiments where a detector receives light from light sources coupled to the system and from light sources not coupled to the system, the detected ambient signal may include the light from the light sources not coupled to the system. Ambient light sources may include sunlight, incandescent room lights, fluorescent room lights, fireplaces, candles, naked flames, LED room lights, instrument panel lighting, heat sources, any other suitable light sources not intended for determining a physiological parameter, or any combination thereof. It will be understood that heat sources may generate non-visible IR light that may be detected by the system. It will be understood that any visible or non-visible source of electromagnetic radiation may be included in the detected ambient signal including, for example, radio waves, microwave, IR, visible, UV, X-ray, gamma ray. In some arrangements, the detected ambient signal may include decaying LED light from the system light sources. For example, it may take a particular amount of time for the light output from a light source to decrease to zero following the light drive signal being switched off. A portion of this emitted light may be included in the detected ambient signal. In some arrangements, the detected ambient signal may not contain physiological information.

As will be described in detail below, a detected light signal may include information related to the amount of light a detector receives when one or more associated light sources are in an "on" state. In some embodiments where a detector receives light from light sources coupled to the system and from light sources not coupled to the system, the detected light signal may include light from both sources. Detected light signals may be time division demultiplexed in a drive pulse modulation or other suitable technique. As described above, a detected light signal may include both a detected emitted photonic signal component and an ambient signal component. In some embodiments, an ambient signal may be subtracted or otherwise separated from a detected light signal. In some embodiments, a detected light signal baseline may be identified based on the detected light signal and the detected ambient signal.

In some embodiments, a sensor may be configured to limit the amount of ambient light received by a detector. For example, a detector may be held close to and facing the skin. A detector may include a light blocking material between the detector and any ambient light sources, to prevent or reduce ambient light from reaching the detector. In a further example, a system may include other suitable shields, optics, filters, arrangements, or any combination thereof, to reduce ambient light signals received by the receiver. In some embodiments, the particular arrangement of light blocking structures or material may depend on the type of probe. For example, a forehead probe may include a relatively flat light blocking structure, while a fingertip probe may include a light blocking structure that encircles the finger. It will be understood, however, that may clinical settings include relatively bright light sources and the ambient light signals received by the detector may not be fully blocked when the sensor is positioned as desired. Similarly, fully shielding ambient light may be more difficult for a forehead sensor than, for example, a fingertip sensor.

In some embodiments, for example, with a fingertip sensor where light may be generated by the system on one side of a finger and detected on the opposite side of a finger, removing the finger from the sensor (i.e., a probe-off condition) may result in a large portion of the generated light being received by the sensor, rather than a portion of the light being attenuated by interacting with the tissue of the subject. This very high signal level may be detected as a probe-off condition by the system.

In some embodiments, for example, with a forehead sensor, a probe-off condition may not result in a relatively high detected signal level. A forehead sensor may include a light source placed relatively close to a detector on the forehead of a patient using tape, an adhesive, a band encircling the skull, any other suitable arrangement, or any combination thereof. The light source and detector may be arranged such that a portion of the light emitted from the light source interacts with, and is partially attenuated by, the tissue of the subject and is detected by the detector. The light source may be pulsed, such that a detected ambient signal is detected by the detector between the pulses, and a detected light signal is detected during the pulses including both a detected ambient light signal and a detected emitted photonic signal. In determining a physiological parameter, the detected ambient light signal may be, for example, subtracted from the detected light signal. The detected ambient signal may exhibit certain characteristic behavior during a probe-off condition, but may remain relatively constant with respect to other changes. For example, during a probe-off condition, the detected ambient light signal may be relatively insensitive to changes in physiological conditions.

In some embodiments, the system may analyze a first signal and a second signal to identify similar behavior. For example, a level or trend of the detected ambient signal may be compared to a level or trend of a detected light signal (e.g., an IR signal). In some embodiments, the detected light signal may include light from a red light emitting diode, an infrared light emitting diode, ambient light, any other suitable light source, or any combination thereof.

In some embodiments, a detected light signal (e.g., an IR signal) and a detected ambient signal may have similar or equal amplitudes. This may be referred to as mimicking-equal behavior. In some embodiments, the system may identify mimicking-equal behavior as being indicative of a probe-off condition. This may occur, for example, when only ambient light is reaching the detector. In this case, the detected ambient and detected light signals are of the same level because they both correspond to the ambient light level. That is to say, the same amount of light is reaching the detector during the "on" and "off" states of the emitters. Mimicking-equal behavior may be identified, for example, when the subtracted difference of one signal from the other is constant within a particular tolerance.

In some embodiments, a detected light signal (e.g., an IR signal) and a detected ambient signal may show similar or parallel variations, referred to as mimicking-parallel behavior. This may be identified, for example, when a first signal is subtracted from a second signal and the result is substantially constant. The difference may be evaluated by its derivative, by changes within a time window, by any other suitable technique, or any combination thereof. In some embodiments, the system may identify mimicking-parallel behavior as being indicative of a probe-off condition.

In some embodiments, two signals may vary in a substantially similar manner but the amplitude of a first signal may change more significantly than the amplitude of a second. For example, this behavior may be exemplified where a first signal subtracted from the product of a second signal and an appropriate scaling factor is equal to zero. This may be referred to as nonlinear scaling. Nonlinear scaling may occur when, for example, mimicking-parallel or mimicking-equal behavior might occur, but one signal displays relatively higher amplitude variations as a result of emitter nonlinearity, detector nonlinearity, gain nonlinearity, processing nonlinearity, other suitable signal variations, or any combination thereof. In some embodiments, the system may identify mimicking with nonlinear scaling as being indicative of a probe-off condition.

In some embodiments, a signal may include a substantially constant amplitude. The substantially constant amplitude may, for example, be identified by the derivative of a signal within a time window. This substantially constant amplitude may be referred to as flatness. In some embodiments, the system may identify flatness as being indicative of a probe-off condition. For example, a detected light signal from a properly positioned probe may normally fluctuate with patient physiological parameters, and thus flatness may indicate that the probe is not properly positioned. Flatness may be identified in a detected light signal, a detected ambient signal, any other suitable signal, or any combination thereof.

It will be understood that any of the aforementioned signal behaviors may be used in any suitable combination. For example, a change in the level of the ambient light (e.g., an examination light is switched on) may be distinguished from a probe-off condition by comparing multiple signal levels, by a trend, by a rate of change, by user input, by any other suitable technique, or any combination thereof. It will also be understood that the aforementioned signal behaviors are merely exemplary and that any suitable signal characteristics or combinations of characteristics may be used to identify a probe-off condition. In further examples, probe-off condition characteristics may include strong ambient light, weak detected light signals, and boundary phase offset conditions.

The foregoing probe-off techniques may be implemented in an oximeter. An oximeter is a medical device that may determine the oxygen saturation of an analyzed tissue. One common type of oximeter is a pulse oximeter, which may non-invasively measure the oxygen saturation of a patient's blood (as opposed to measuring oxygen saturation directly by analyzing a blood sample taken from the patient). Pulse oximeters may be included in patient monitoring systems that measure and display various blood flow characteristics including, but not limited to, the oxygen saturation of hemoglobin in arterial blood. Such patient monitoring systems may also measure and display additional physiological parameters, such as a patient's pulse rate and blood pressure.

An oximeter may include a light sensor that is placed at a site on a patient, typically a fingertip, toe, forehead or earlobe, or in the case of a neonate, across a foot or hand. The oximeter may use a light source to pass light through blood perfused tissue and photoelectrically sense the absorption of the light in the tissue. In addition, locations which are not typically understood to be optimal for pulse oximetry serve as suitable sensor locations for the blood pressure monitoring processes described herein, including any location on the body that has a strong pulsatile arterial flow. For example, additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, and around or in front of the ear. Suitable sensors for these locations may include sensors for sensing absorbed light based on detecting reflected light. In all suitable locations, for example, the oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters, including an amount of a blood constituent (e.g., oxyhemoglobin) being measured as well as a pulse rate and when each individual pulse occurs.

In some embodiments, the photonic signal interacting with the tissue is selected to be of one or more wavelengths that are attenuated by the blood in an amount representative of the blood constituent concentration. Red and infrared (IR) wavelengths may be used because it has been observed that highly oxygenated blood will absorb relatively less red light and more IR light than blood with a lower oxygen saturation. By comparing the intensities of two wavelengths at different points in the pulse cycle, it is possible to estimate the blood oxygen saturation of hemoglobin in arterial blood.

The system may process data to determine physiological parameters using techniques well known in the art. For example, the system may determine blood oxygen saturation using two wavelengths of light and a ratio-of-ratios calculation. The system also may identify pulses and determine pulse amplitude, respiration, blood pressure, other suitable parameters, or any combination thereof, using any suitable calculation techniques. In some embodiments, the system may use information from external sources (e.g., tabulated data, secondary sensor devices) to determine physiological parameters.

In some embodiments, a light drive modulation may be used. For example, a first light source may be turned on for a first drive pulse, followed by an off period, followed by a second light source for a second drive pulse, followed by an off period. The first and second drive pulses may be used to determine physiological parameters. The off periods may be used to determine detected ambient signal levels, reduce overlap of the light drive pulses, allow time for light sources to stabilize, allow time for detected light signals to stabilize or settle, reduce heating effects, reduce power consumption, for any other suitable reason, or any combination thereof.

It will be understood that the probe-off techniques described herein are not limited to pulse oximeters and may be applied to any suitable medical and non-medical devices. For example, the system may include probes for regional saturation (rSO2), respiration rate, respiration effort, continuous non-invasive blood pressure, saturation pattern detection, fluid responsiveness, cardiac output, any other suitable clinical parameter, or any combination thereof. Probes may be used with a pulse oximeter, a general purpose medical monitor, any other suitable medical device, or any combination thereof. In some embodiments, the probe-off identification techniques described herein may be applied to analysis of light levels where an ambient or dark signal is detected.

The following description and accompanying FIGS. 1-10 provide additional details and features of some embodiments of determining a sensor condition in a medical device.

FIG. 1 is a block diagram of an illustrative physiological monitoring system 100 in accordance with some embodiments of the present disclosure. System 100 may include a sensor 102 and a monitor 104 for generating and processing physiological signals of a subject. In some embodiments, sensor 102 and monitor 104 may be part of an oximeter.

Sensor 102 of physiological monitoring system 100 may include light source 130 and detector 140. Light source 130 may be configured to emit photonic signals having one or more wavelengths of light (e.g. Red and IR) into a subject's tissue. For example, light source 130 may include a Red light emitting light source and an IR light emitting light source, e.g. Red and IR light emitting diodes (LEDs), for emitting light into the tissue of a subject to generate physiological signals. In one embodiment, the Red wavelength may be between about 600 nm and about 700 nm, and the IR wavelength may be between about 800 nm and about 1000 nm. It will be understood that light source 130 may include any number of light sources with any suitable characteristics. In embodiments where an array of sensors is used in place of single sensor 102, each sensor may be configured to emit a single wavelength. For example, a first sensor may emit only a Red light while a second may emit only an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 140 may be chosen to be specifically sensitive to the chosen targeted energy spectrum of light source 130.

In some embodiments, detector 140 may be configured to detect the intensity of light at the Red and IR wavelengths. In some embodiments, an array of sensors may be used and each sensor in the array may be configured to detect an intensity of a single wavelength. In operation, light may enter detector 140 after passing through the subject's tissue. Detector 140 may convert the intensity of the received light into an electrical signal. The light intensity may be directly related to the absorbance and/or reflectance of light in the tissue. That is, when more light at a certain wavelength is absorbed, scattered, or reflected, less light of that wavelength is typically received from the tissue by detector 140. After converting the received light to an electrical signal, detector 140 may send the detection signal to monitor 104, where the detection signal may be processed and physiological parameters may be determined (e.g., based on the absorption of the Red and IR wavelengths in the subject's tissue). In some embodiments, the detection signal may be preprocessed by sensor 102 before being transmitted to monitor 104.

In the embodiment shown, monitor 104 includes control circuitry 110, light drive circuitry 120, front end processing circuitry 150, back end processing circuitry 170, user interface 180, and communication interface 190. Monitor 104 may be communicatively coupled to sensor 102.

Control circuitry 110 may be coupled to light drive circuitry 120, front end processing circuitry 150, and back end processing circuitry 170, and may be configured to control the operation of these components. In some embodiments, control circuitry 110 may be configured to provide timing control signals to coordinate their operation. For example, light drive circuitry 120 may generate a light drive signal, which may be used to turn on and off the light source 130, based on the timing control signals. The front end processing circuitry 150 may use the timing control signals of control circuitry 110 to operate synchronously with light drive circuitry 120. For example, front end processing circuitry 150 may synchronize the operation of an analog-to-digital converter and a demultiplexer with the light drive signal based on the timing control signals. In addition, the back end processing circuitry 170 may use the timing control signals of control circuitry 110 to coordinate its operation with front end processing circuitry 150.

Light drive circuitry 120, as discussed above, may be configured to generate a light drive signal that is provided to light source 130 of sensor 102. The light drive signal may, for example, control the intensity of light source 130 and the timing of switching light source 130 on and off. When light source 130 is configured to emit two or more wavelengths of light, the light drive signal may be configured to control the operation of each wavelength of light. The light drive signal may comprise a single signal or may comprise multiple signals (e.g., one signal for each wavelength of light). An illustrative light drive signal is shown in FIG. 2A.

Figure 2A:
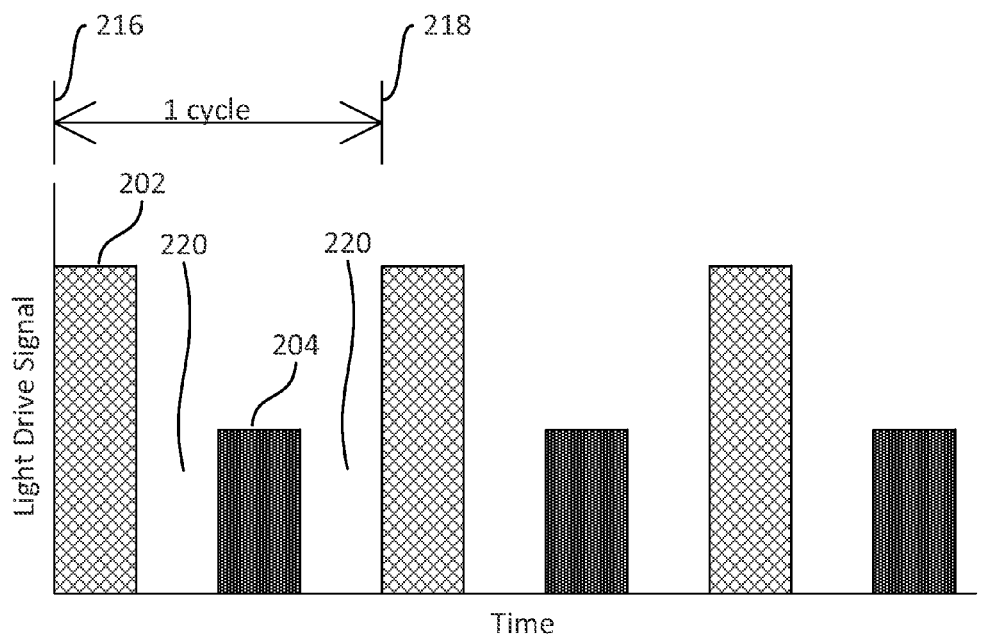
FIG. 2A shows an illustrative plot of a light drive signal including a red drive pulse and an IR drive pulse in accordance with some embodiments of the present disclosure.

FIG. 2A shows an illustrative plot of a light drive signal including red drive pulse 202 and IR drive pulse 204 in accordance with some embodiments of the present disclosure. Red drive pulse 202 and IR drive pulse 204 may be generated by light drive circuitry 120 under the control of control circuitry 110. As used herein, drive pulses may refer to switching power or other components on and off, high and low output states, high and low values within a continuous modulation, other suitable relatively distinct states, or any combination thereof. The light drive signal may be provided to light source 130, including red drive pulse 202 and IR drive pulse 204 to drive red and IR light emitters, respectively, within light source 130. Red drive pulse 202 may have a higher amplitude than IR drive pulse 204 since red LEDs may be less efficient than IR LEDs at converting electrical energy into light energy. In some embodiments, the output levels may be the equal, may be adjusted for nonlinearity of emitters, may be modulated in any other suitable technique, or any combination thereof. Additionally, red light may be absorbed and scattered more than IR light when passing through perfused tissue. When the red and IR light sources are driven in this manner they emit pulses of light at their respective wavelengths into the tissue of a subject in order generate physiological signals that physiological monitoring system 100 may process to calculate physiological parameters. It will be understood that the light drive amplitudes of FIG. 2A are merely exemplary any that any suitable amplitudes or combination of amplitudes may be used, and may be based on the light sources, the subject tissue, the determined physiological parameter, modulation techniques, power sources, any other suitable criteria, or any combination thereof.

The light drive signal of FIG. 2A may also include "off" periods 220 between the Red and IR light drive pulse. "Off" periods 220 are periods during which no drive current may be applied to light source 130. "Off" periods 220 may be provided, for example, to prevent overlap of the emitted light, since light source 130 may require time to turn completely on and completely off. Similarly, the signal from detector 140 may require time to decay completely to a final state after light source 130 is switched off. The period from time 216 to time 218 may be referred to as a drive cycle, which includes four segments: a red drive pulse 202, followed by an "off" period 220 in FIG. 2A, followed by an IR drive pulse 204, and followed by an "off" period 220. After time 218, the drive cycle may be repeated (e.g., as long as a light drive signal is provided to light source 130). It will be understood that the starting point of the drive cycle is merely illustrative and that the drive cycle can start at any location within FIG. 2A, provided the cycle spans two drive pulses and two "off" periods. Thus, each red drive pulse 202 and each IR drive pulse 204 may be understood to be surrounded by two "off"

periods 220 in FIG. 2A. "Off" periods may also be referred to as dark periods, in that the emitters are dark or returning to dark during that period.

Referring back to FIG. 1, front end processing circuitry 150 may receive a detection signal from detector 140 and provide one or more processed signals to back end processing circuitry 170. The term "detection signal," as used herein, may refer to any of the signals generated within front end processing circuitry 150 as it processes the output signal of detector 140. Front end processing circuitry 150 may perform various analog and digital processing of the detector signal. One suitable detector signal that may be received by front end processing circuitry 150 is shown in FIG. 2B.

Figure 2B:
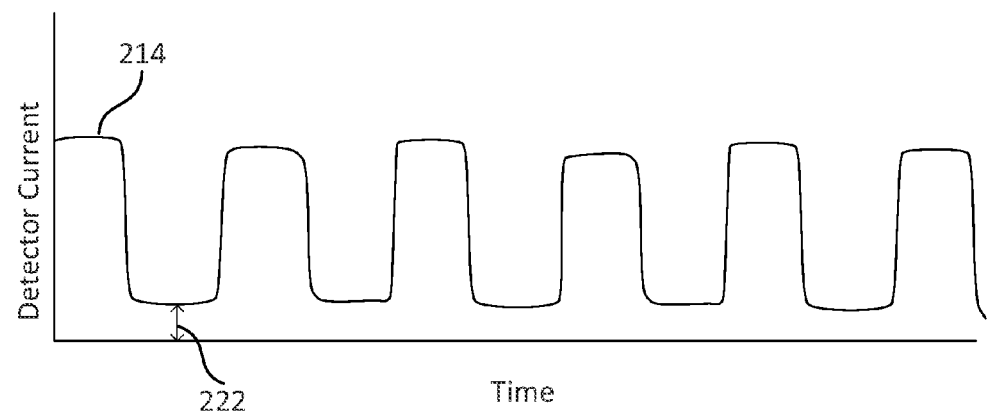
FIG. 2B shows an illustrative plot of a detector current waveform that may be generated by a sensor in accordance with some embodiments of the present disclosure.

FIG. 2B shows an illustrative plot of detector current waveform 214 that may be generated by a sensor in accordance with some embodiments of the present disclosure. The peaks of detector current waveform 214 may represent current signals provided by a detector, such as detector 140 of FIG. 1, when light is being emitted from a light source. The amplitude of detector current waveform 214 may be proportional to the light incident upon the detector. The peaks of detector current waveform 214 may be synchronous with drive pulses driving one or more emitters of a light source, such as light source 130 of FIG. 1. For example, detector current waveform 214 may be generated in response to a light source being driven by the light drive signal of FIG. 2A. The valleys of detector current waveform 214 may be synchronous with periods of time during which no light is being emitted by the light source. While no light is being emitted by a light source during the valleys, detector current waveform 214 may not decrease to zero. Rather, ambient signal 222 may be present in the detector waveform, as well as other background amplitude contributions. In some embodiments, the shapes of the pulses in detector current waveforms may include distortions, clipping, delayed switching, relatively slow rising and falling edges, and other non-idealities due in part to switching of the light drive, switching of the LEDs, switching in the detector, stabilization of the detector, stabilization of the detected signal, parasitic inductance and/or capacitances, any other suitable signal contribution, or any combination thereof. In some embodiments, ambient signal 222 may be used to determine a probe-off condition. In some embodiments, ambient signal 222 may be removed from a processed signal to facilitate determination of physiological parameters.

Referring back to FIG. 1, front end processing circuitry 150, which may receive a detection signal, such as detector current waveform 214, may include analog conditioner 152, demultiplexer 154, digital conditioner 156, analog-to-digital converter (ADC) 158, decimator/interpolator 160, and ambient subtractor 162.

In some embodiments, front end processing circuitry 150 may include a second analog-to-digital converter (not shown) configured to sample the unprocessed detector signal. This signal may be used to detect changes in the ambient light level without applying the signal condition and other steps that may improve the quality of determined physiological parameters but may reduce the amount of information regarding a probe-off condition.

Analog conditioner 152 may perform any suitable analog conditioning of the detector signal. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof.

The conditioned analog signal may be processed by analog-to-digital converter 158, which may convert the conditioned analog signal into a digital signal. Analog-to-digital converter 158 may operate under the control of control circuitry 110. Analog-to-digital converter 158 may use timing control signals from control circuitry 110 to determine when to sample the analog signal. Analog-to-digital converter 158 may be any suitable type of analog-to-digital converter of sufficient resolution to enable a physiological monitor to accurately determine physiological parameters.

Demultiplexer 154 may operate on the analog or digital form of the detector signal to separate out different components of the signal. For example, detector current waveform 214 of FIG. 2B includes a Red component, an IR component, and at least one ambient component. Demultiplexer 154 may operate on detector current waveform 214 of FIG. 2B to generate a Red signal, an IR signal, a first ambient signal (e.g., corresponding to the ambient component that occurs immediately after the Red component), and a second ambient signal (e.g., corresponding to the ambient component that occurs immediately after the IR component). Demultiplexer 154 may operate under the control of control circuitry 110. For example, demultiplexer 154 may use timing control signals from control circuitry 110 to identify and separate out the different components of the detector signal.

Digital conditioner 156 may perform any suitable digital conditioning of the detector signal. Digital conditioner 156 may include any type of digital filtering of the signal (e.g., low pass, high pass, band pass, notch, or any other suitable filtering), amplifying, performing an operation on the signal, performing any other suitable digital conditioning, or any combination thereof.

Decimator/interpolator 160 may decrease the number of samples in the digital detector signal. For example, decimator/interpolator 160 may decrease the number of samples by removing samples from the detector signal or replacing samples with a smaller number of samples. The decimation or interpolation operation may include or be followed by filtering to smooth the output signal.

Ambient subtractor 162 may operate on the digital signal. In some embodiments, ambient subtractor 162 may remove ambient values from the Red and IR components. In some embodiments, the system may subtract the ambient values from the Red and IR components to generate adjusted Red and IR signals. For example, ambient subtractor 162 may determine a subtraction amount from the ambient signal portion of the detection signal and subtract it from the peak portion of the detection signal in order to reduce the effect of the ambient signal on the peak. For example, in reference to FIG. 2A, a detection signal peak corresponding to red drive pulse 202 may be adjusted by determining the amount of ambient signal during the "off" period 220 preceding red drive pulse 202. The ambient signal amount determined in this manner may be subtracted from the detector peak corresponding to red drive pulse 202. Alternatively, the "off" period 220 after red drive pulse 202 may be used to correct red drive pulse 202 rather than the "off" period 220 preceding it. Additionally, an average of the "off" periods 220 before and after "on" periods of red drive pulse 202 may be used. In some embodiments, ambient subtractor 162 may output an ambient signal for further processing. Ambient subtractor 162 may average the ambient signal from multiple "off" periods 220, may apply filters to the ambient signal such as averaging filters, integration filters, delay filters, buffers, counters, any other suitable filters or processing, or any combination thereof.

It will be understood that in some embodiments, ambient subtractor 162 may be omitted. It will also be understood that in some embodiments, the system may not subtract the ambient contribution of the signal. It will also be understood that the functions of demultiplexer 154 and ambient subtractor 162 may be complementary, overlapping, combined into a signal function, combined or separated in any suitable arrangement, or any combination thereof. For example, the received light signal may include an ambient signal, an IR light signal, and a red light signal. The system may use any suitable arrangement of demultiplexer 154 and ambient subtractor 162 to determine or generate any combination of: a red signal, an IR signal, a red ambient signal, an IR ambient signal, an average ambient signal, a red with ambient signal, an IR with ambient signal, any other suitable signal, or any combination thereof.

The components of front end processing circuitry 150 are merely illustrative and any suitable components and combinations of components may be used to perform the front end processing operations.

The front end processing circuitry 150 may be configured to take advantage of the full dynamic range of analog-to-digital converter 158. This may be achieved by applying a gain to the detected signal using analog conditioner 152 to map the expected range of the detection signal to the full or close to full dynamic range of analog-to-digital converter 158. In some embodiments, the input to the analog to digital converter may be the sum of the detected light multiplied by an analog gain value.

Ideally, when ambient light is zero and when the light source is off, the analog-to-digital converter 158 will read just above the minimum input value. When the light source is on, the total analog gain may be set such that the output of analog-to-digital converter 158 may read close to the full scale of analog-to-digital converter 158 without saturating. This may allow the full dynamic range of analog-to-digital converter 158 to be used for representing the detection signal, thereby increasing the resolution of the converted signal. In some embodiments, the total analog gain may be reduced by a small amount so that small changes in the light level incident on the detector do not cause saturation of analog-to-digital converter 158.

Back end processing circuitry 170 may include processor 172 and memory 174. Processor 172 may be adapted to execute software, which may include an operating system and one or more applications, as part of performing the functions described herein. Processor 172 may receive and further process physiological signals received from front end processing circuitry 150. For example, processor 172 may determine one or more physiological parameters based on the received physiological signals. Memory 174 may include any suitable computer-readable media capable of storing information that can be interpreted by processor 172. This information may be data or may take the form of computer-executable instructions, such as software applications, that cause the microprocessor to perform certain functions and/or computer-implemented methods. Depending on the embodiment, such non-transitory computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system. Back end processing circuitry 170 may be communicatively coupled with user interface 180 and communication interface 190.

User interface 180 may include user input 182, display 184, and speaker 186. User input 182 may include any type of user input device such as a keyboard, a mouse, a touch screen, buttons, switches, a microphone, a joy stick, a touch pad, or any other suitable input device. The inputs received by user input 182 can include information about the subject, such as age, weight, height, diagnosis, medications, treatments, and so forth. In an embodiment, the subject may be a medical patient and display 184 may exhibit a list of values which may generally apply to the patient, such as, for example, age ranges or medication families, which the user may select using user inputs 182. Additionally, display 184 may display, for example, an estimate of a subject's blood oxygen saturation generated by monitor 104 (referred to as an "$SpO_2$" measurement), pulse rate information, respiration rate information, blood pressure, sensor condition, any other parameters, and any combination thereof. Display 184 may include any type of display such as a cathode ray tube display, a flat panel display such a liquid crystal display or plasma display, or any other suitable display device. Speaker 186 within user interface 180 may provide an audible sound that may be used in various embodiments, such as for example, sounding an audible alarm in the event that a patient's physiological parameters are not within a predefined normal range.

Communication interface 190 may enable monitor 104 to exchange information with external devices. Communication interface 190 may include any suitable hardware, software, or both, which may allow monitor 104 to communicate with electronic circuitry, a device, a network, a server or other workstations, a display, or any combination thereof. Communication interface 190 may include one or more receivers, transmitters, transceivers, antennas, plug-in connectors, ports, communications buses, communications protocols, device identification protocols, any other suitable hardware or software, or any combination thereof. Communication interface 190 may be configured to allow wired communication (e.g., using USB, RS-232 or other standards), wireless communication (e.g., using WiFi, IR, WiMax, BLUETOOTH, UWB, or other standards), or both. For example, communication interface 190 may be configured using a universal serial bus (USB) protocol (e.g., USB 2.0, USB 3.0), and may be configured to couple to other devices (e.g., remote memory devices storing templates) using a four-pin USB standard Type-A connector (e.g., plug and/or socket) and cable. In some embodiments, communication interface 190 may include an internal bus such as, for example, one or more slots for insertion of expansion cards.

It will be understood that the components of physiological monitoring system 100 that are shown and described as separate components are shown and described as such for illustrative purposes only. In some embodiments the functionality of some of the components may be combined in a single component. For example, the functionality of front end processing circuitry 150 and back end processing circuitry 170 may be combined in a single processor system. Additionally, in some embodiments the functionality of some of the components of monitor 104 shown and described herein may be divided over multiple components. For example, some or all of the functionality of control circuitry 110 may be performed in front end processing circuitry 150, in back end processing circuitry 170, or both. In other embodiments, the functionality of one or more of the components may be performed in a different order or may not be required. In some embodiments, all of the components of physiological monitoring system 100 can be realized in processor circuitry.

Figure 3:
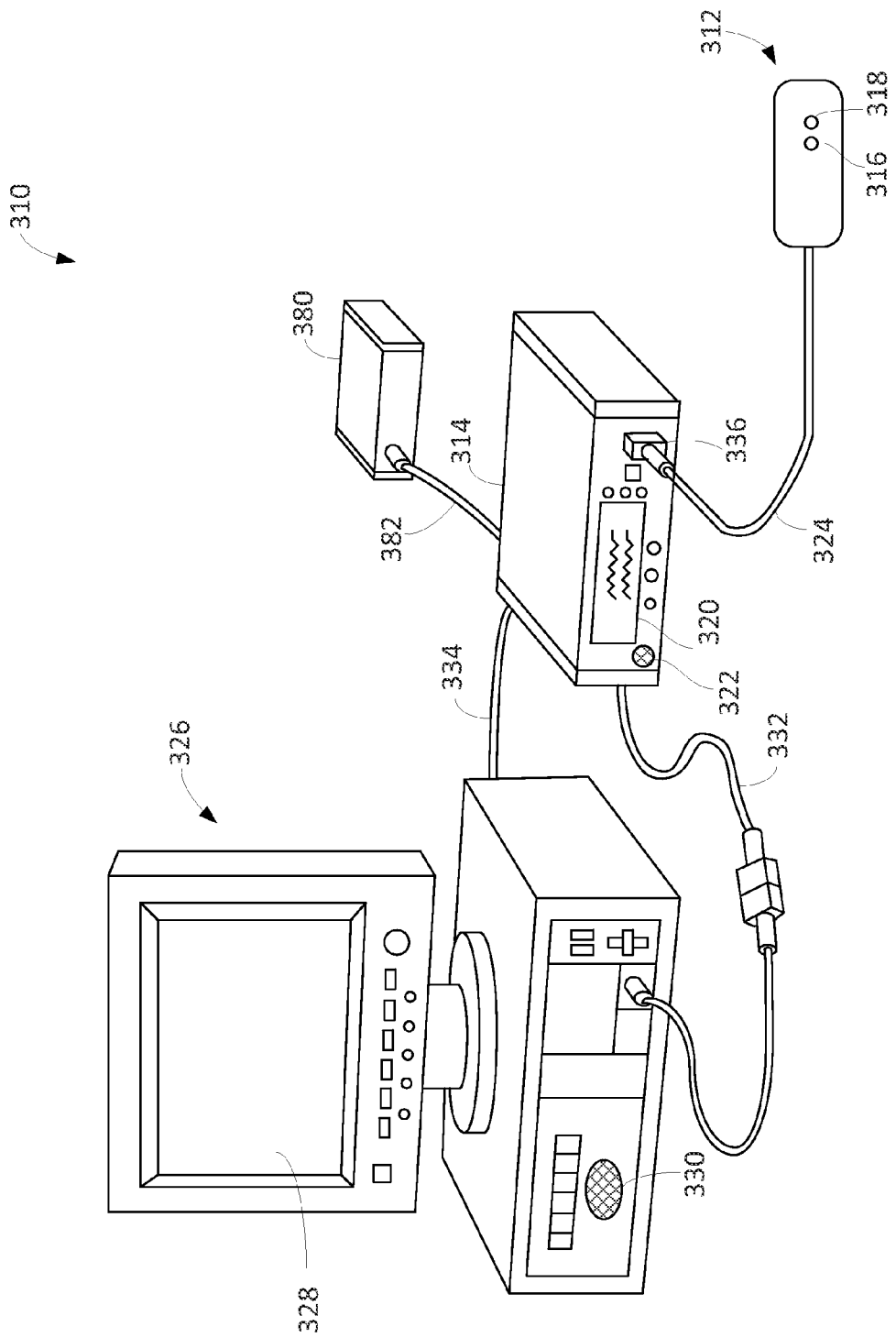
FIG. 3 is a perspective view of an embodiment of a physiological monitoring system in accordance with some embodiments of the present disclosure.

FIG. 3 is a perspective view of an embodiment of a physiological monitoring system 310 in accordance with some embodiments of the present disclosure. In some embodiments, one or more components of physiological monitoring system 310 may include one or more components of physiological monitoring system 100 of FIG. 1. Physiological monitoring system 310 may include sensor unit 312 and monitor 314. In some embodiments, sensor unit 312 may be part of an oximeter. Sensor unit 312 may include one or more light source 316 for emitting light at one or more wavelengths into a subject's tissue. One or more detectors 318 may also be provided in sensor unit 312 for detecting the light that is reflected by or has traveled through the subject's tissue. Any suitable configuration of light source 316 and detector 318 may be used. In an embodiment, sensor unit 312 may include multiple light sources and detectors, which may be spaced apart. Physiological monitoring system 310 may also include one or more additional sensor units (not shown) that may, for example, take the form of any of the embodiments described herein with reference to sensor unit 312. An additional sensor unit may be the same type of sensor unit as sensor unit 312, or a different sensor unit type than sensor unit 312 (e.g., a photoacoustic sensor). Multiple sensor units may be capable of being positioned at two or more different locations on a subject's body.

In some embodiments, sensor unit 312 may be connected to monitor 314 as shown. Sensor unit 312 may be powered by an internal power source, e.g., a battery (not shown). Sensor unit 312 may draw power from monitor 314. In another embodiment, the sensor may be wirelessly connected to monitor 314 (not shown). Monitor 314 may be configured to calculate physiological parameters based at least in part on data relating to light emission and detection received from one or more sensor units such as sensor unit 312. For example, monitor 314 may be configured to determine pulse rate, blood pressure, blood oxygen saturation (e.g., arterial, venous, or both), hemoglobin concentration (e.g., oxygenated, deoxygenated, and/or total), any other suitable physiological parameters, or any combination thereof. In some embodiments, calculations may be performed on the sensor units or an intermediate device and the result of the calculations may be passed to monitor 314. Further, monitor 314 may include display 320 configured to display the physiological parameters or other information about the system. In the embodiment shown, monitor 314 may also include a speaker 322 to provide an audible sound that may be used in various other embodiments, such as for example, sounding an audible alarm in the event that a subject's physiological parameters are not within a predefined normal range or when a sensor is not properly positioned. In some embodiments, physiological monitoring system 310 may include a stand-alone monitor in communication with the monitor 314 via a cable or a wireless network link. In some embodiments, monitor 314 may be implemented as display 184 of FIG. 1.

In some embodiments, sensor unit 312 may be communicatively coupled to monitor 314 via a cable 324. Cable 324 may include electronic conductors (e.g., wires for transmitting electronic signals from detector 318), optical fibers (e.g., multi-mode or single-mode fibers for transmitting emitted light from light source 316), any other suitable components, any suitable insulation or sheathing, or any combination thereof. In some embodiments, a wireless transmission device (not shown) or the like may be used instead of or in addition to cable 324. Monitor 314 may include a sensor interface configured to receive physiological signals from sensor unit 312, provide signals and power to sensor unit 312, or otherwise communicate with sensor unit 312. The sensor interface may include any suitable hardware, software, or both, which may be allow communication between monitor 314 and sensor unit 312.

In some embodiments, physiological monitoring system 310 may include calibration device 380. Calibration device 380, which may be powered by monitor 314, a battery, or by a conventional power source such as a wall outlet, may include any suitable calibration device. Calibration device 380 may be communicatively coupled to monitor 314 via communicative coupling 382, and/or may communicate wirelessly (not shown). In some embodiments, calibration device 380 is completely integrated within monitor 314. In some embodiments, calibration device 380 may include a manual input device (not shown) used by an operator to manually input reference signal measurements obtained from some other source (e.g., an external invasive or non-invasive physiological measurement system).

In the illustrated embodiment, physiological monitoring system 310 includes a multi-parameter physiological monitor 326. The display 328 of multi-parameter physiological monitor 326 may include a cathode ray tube display, a flat panel display (as shown) such as a liquid crystal display (LCD) or a plasma display, or may include any other type of monitor now known or later developed. Multi-parameter physiological monitor 326 may be configured to calculate physiological parameters and to provide information from monitor 314 and from other medical monitoring devices or systems (not shown) using display 328. For example, multi-parameter physiological monitor 326 may be configured to display an estimate of a subject's blood oxygen saturation and hemoglobin concentration generated by monitor 314. Multi-parameter physiological monitor 326 may include a speaker 330.

Monitor 314 may be communicatively coupled to multi-parameter physiological monitor 326 via a cable 332 or 334 that is coupled to a sensor input port or a digital communications port, respectively and/or may communicate wirelessly (not shown). In addition, monitor 314 and/or multi-parameter physiological monitor 326 may be coupled to a network to enable the sharing of information with servers or other workstations (not shown). Monitor 314 may be powered by a battery (not shown) or by a conventional power source such as a wall outlet.

In some embodiments, all or some of monitor 314 and multi-parameter physiological monitor 326 may be referred to collectively as processing equipment.

Figure 4:
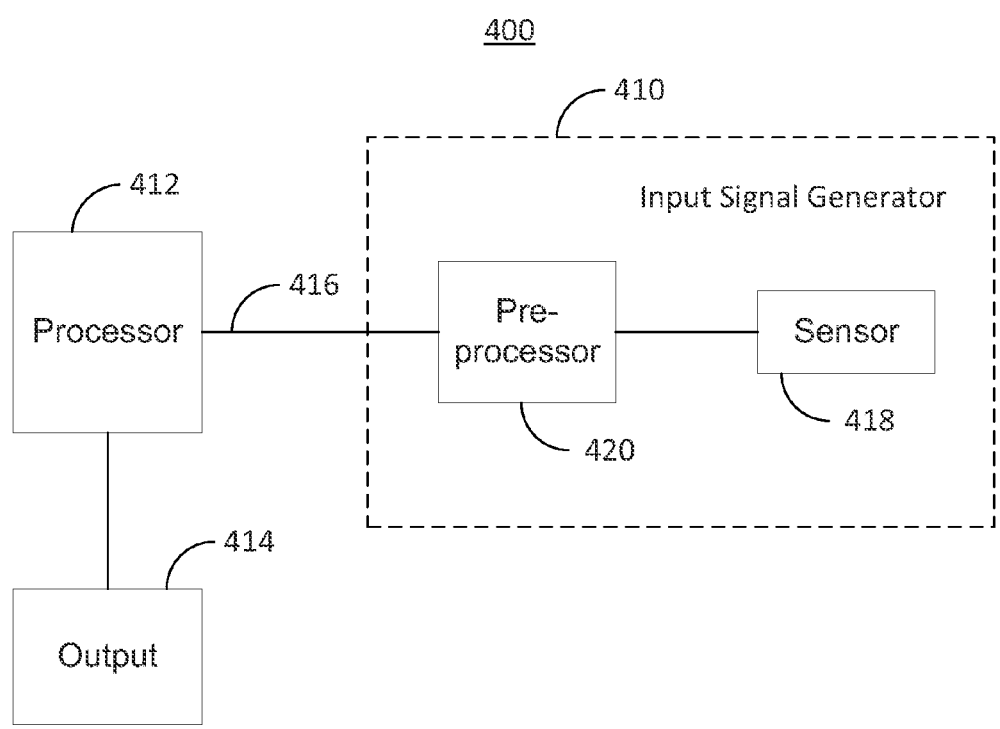
FIG. 4 shows an illustrative signal processing system in accordance with some embodiments of the present disclosure.

FIG. 4 shows illustrative signal processing system 400 in accordance with some embodiments of the present disclosure. Signal processing system 400 includes input signal generator 410, processor 412 and output 414. In the illustrated embodiment, input signal generator 410 may include pre-processor 420 coupled to sensor 418. As illustrated, input signal generator 410 generates an input signal 416. In some embodiments, input signal 416 may include one or more intensity signals based on a detector output. In some embodiments, pre-processor 420 may be an oximeter and input signal 416 may be a PPG signal. In an embodiment, pre-processor 420 may be any suitable signal processing device and input signal 416 may include PPG signals and one or more other physiological signals, such as an electrocardiogram (ECG) signal. It will be understood that input signal generator 410 may include any suitable signal source, signal generating data, signal generating equipment, or any combination thereof to produce input signal 416. Input signal 416 may be a single signal, or may be multiple signals transmitted over a single pathway or multiple pathways.

Pre-processor 420 may apply one or more signal processing operations to the signal generated by sensor 418. For example, pre-processor 420 may apply a pre-determined set of processing operations to the signal provided by sensor 418 to produce input signal 416 that can be appropriately interpreted by processor 412, such as performing A/D conversion. In some embodiments, A/D conversion may be performed by processor 412. Pre-processor 420 may also perform any of the following operations on the signal provided by sensor 418: reshaping the signal for transmission, multiplexing the signal, modulating the signal onto carrier signals, compressing the signal, encoding the signal, and filtering the signal. In some embodiments, pre-processor 420 may include a current-to-voltage converter (e.g., to convert a photocurrent into a voltage), an amplifier, a filter, and A/D converter, a de-multiplexer, any other suitable pre-processing components, or any combination thereof. In some embodiments, pre-processor 420 may include one or more components from front end processing circuitry 150 of FIG. 1.

In some embodiments, input signal 416 may include PPG signals corresponding to one or more light frequencies, such as an IR PPG signal and a Red PPG signal, and ambient light. In some embodiments, input signal 416 may include signals measured at one or more sites on a subject's body, for example, a subject's finger, toe, ear, arm, or any other body site. In some embodiments, input signal 416 may include multiple types of signals (e.g., one or more of an ECG signal, an EEG signal, an acoustic signal, an optical signal, a signal representing a blood pressure, and a signal representing a heart rate). Input signal 416 may be any suitable biosignal or any other suitable signal.

In some embodiments, input signal 416 may be coupled to processor 412. Processor 412 may be any suitable software, firmware, hardware, or combination thereof for processing input signal 416. For example, processor 412 may include one or more hardware processors (e.g., integrated circuits), one or more software modules, non-transitory computer-readable media such as memory, firmware, or any combination thereof. Processor 412 may, for example, be a computer or may be one or more chips (i.e., integrated circuits). Processor 412 may, for example, include an assembly of analog electronic components. Processor 412 may calculate physiological information. For example, processor 412 may compute one or more of a pulse rate, respiration rate, blood pressure, or any other suitable physiological parameter. Processor 412 may perform any suitable signal processing of input signal 416 to filter input signal 416, such as any suitable band-pass filtering, adaptive filtering, closed-loop filtering, any other suitable filtering, and/or any combination thereof. Processor 412 may also receive input signals from additional sources (not shown). For example, processor 412 may receive an input signal containing information about treatments provided to the subject. Additional input signals may be used by processor 412 in any of the calculations or operations it performs in accordance with processing system 400.

In some embodiments, all or some of pre-processor 420, processor 412, or both, may be referred to collectively as processing equipment.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store fiducial information or initialization information corresponding to physiological monitoring. In some embodiments, processor 412 may store physiological measurements or previously received data from input signal 416 in a memory device for later retrieval. In some embodiments, processor 412 may store calculated values, such as a pulse rate, a blood pressure, a blood oxygen saturation, a fiducial point location or characteristic, an initialization parameter, or any other calculated values, in a memory device for later retrieval.

Processor 412 may be coupled to output 414. Output 414 may be any suitable output device such as one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into physiological monitoring system 100 of FIG. 1. For example, input signal generator 410 may be implemented as part of sensor 102. In another example, system 400 may be incorporated into physiological monitoring system 310 of FIG. 3, where input signal generator 410 may be implemented as part of sensor unit 312 of FIG. 3. Processor 412 may be implemented as part of monitor 104 of FIG. 1 or as part of monitor 314 or multi-parameter physiological monitor 326 of FIG. 3. Output 414 may be implemented as display 320 or 328 of FIG. 3. Furthermore, all or part of system 400 may be embedded in a small, compact object carried with or attached to the subject (e.g., a watch, other piece of jewelry, or a smart phone). In some embodiments, a wireless transceiver (not shown) may also be included in system 400 to enable wireless communication with other components of physiological monitoring systems 100 of FIG. 1 and 310 of FIG. 3. As such, physiological monitoring systems 100 of FIG. 1 and 310 of FIG. 3 may be part of a fully portable and continuous subject monitoring solution. In some embodiments, a wireless transceiver (not shown) may also be included in system 400 to enable wireless communication with other components of physiological monitoring systems 100 of FIG. 1 and 310 of FIG. 3. For example, pre-processor 420 may communicate input signal 416 over BLUETOOTH, 802.11, WiFi, WiMax, cable, satellite, Infrared, or any other suitable transmission scheme. In some embodiments, a wireless transmission scheme may be used between any communicating components of system 400. In some embodiments, system 400 may include one or more communicatively coupled modules configured to perform particular tasks. In some embodiments, system 400 may be included as a module communicatively coupled to one or more other modules.

It will be understood that the components of signal processing system 400 that are shown and described as separate components are shown and described as such for illustrative purposes only. In other embodiments the functionality of some of the components may be combined in a single component. For example, the functionality of processor 412 and pre-processor 420 may combined in a single processor system. Additionally, the functionality of some of the components shown and described herein may be divided over multiple components. Additionally, signal processing system 400 may perform the functionality of other components not show in FIG. 4. For example, some or all of the functionality of control circuitry 110 of FIG. 1 may be performed in signal processing system 400. In other embodiments, the functionality of one or more of the components may not be required. In an embodiment, all of the components can be realized in processor circuitry.

In some embodiments, any of the processing components and/or circuits, or portions thereof, of FIGS. 1, 3, and 4 may be referred to collectively as processing equipment. For example, processing equipment may be configured to amplify, filter, sample and digitize input signal 416 (e.g., using an analog-to-digital converter), and calculate physiological information from the digitized signal. Processing equipment may be configured to generate light drive signals, amplify, filter, sample and digitize detector signals, and calculate physiological information from the digitized signal. In some embodiments, all or some of the components of the processing equipment may be referred to as a processing module.

Figure 5:
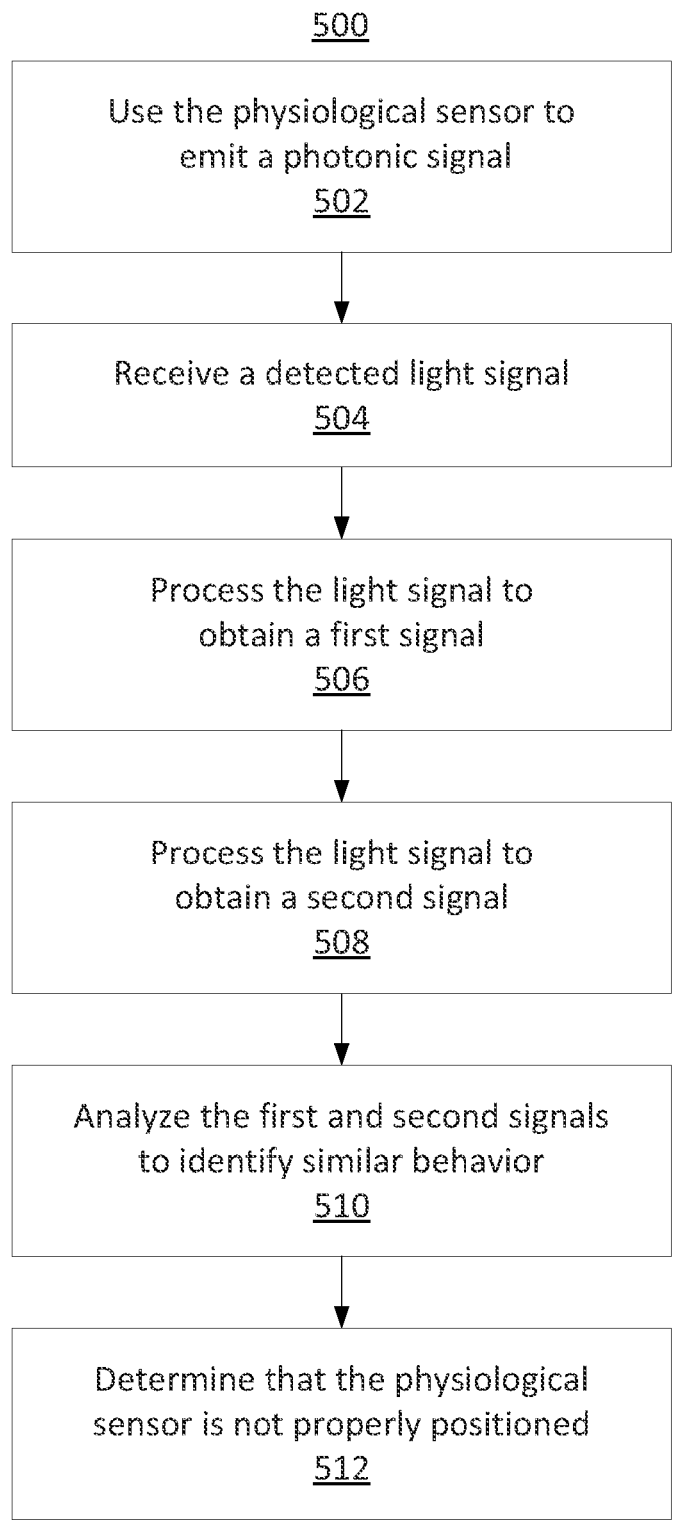
FIG. 5 is a flow diagram showing illustrative steps for determining whether a sensor is properly positioned in accordance with some embodiments of the present disclosure.

FIG. 5 is flow diagram 500 showing illustrative steps for determining whether a sensor is properly positioned in accordance with some embodiments of the present disclosure.

In step 502, the system may use the physiological sensor to emit an emitted photonic signal. The system may emit the emitted photonic signal including one wavelength of light, multiple wavelengths of light, a broad spectrum light (e.g., white light), or any combination thereof. For example, the emitted photonic signal may include light from a red LED and light from an IR LED. The emitted photonic signal may be emitted, for example, by light source 130 of FIG. 1 or light source 316 of FIG. 3. In some embodiments, the emitted photonic signal may include a light drive modulation. For example, when the emitted photonic signal includes a red light source and an IR light source, the light drive modulation may include a red drive pulse followed by an "off" period followed by an IR drive pulse followed by an off period. It will be understood that this drive cycle modulation is merely exemplary and that any suitable drive cycle modulation or combination of modulations may be used. In some embodiments, the emitted photonic signal may include a cardiac cycle modulation, where the brightness, duty cycle, or other parameters of one or more emitters are varied at a rate substantially related to the cardiac cycle.

In step 504, the system may receive a light signal. The received light signal may include the detected light signal and the detected ambient signal, as described above. For example, the detected light signal and the ambient signal may be determined by demultiplexing a received light signal based on time division multiplexing of the emitters. In some embodiments, the received light signal may in part correspond to the emitted photonic signals of step 502, light from ambient light sources, any other suitable source, or any combination thereof. The received light signal may be received by, for example, detector 140 of FIG. 1 or detector 318 of FIG. 3. In some embodiments, a portion of the emitted photonic light signal may be partially attenuated by the tissue of the subject before being detected as a received light signal. In some embodiments, the received light signal may have been primarily reflected by the subject. For example, reflected light may be detected by a forehead-attached system where the emitter and detector are on the same side of the subject. In some embodiments, the received light may be have been transmitted through the subject. For example, transmitted light may be detected in a fingertip-attached or earlobe-attached sensor.

In some embodiments, the system may adjust or compensate a received light signal depending in part on a light drive setting. Drive settings may include the LED drive signal, the detector gain, other suitable system parameters, or any combination thereof. For example, increasing the gain on a detected signal may result in an increased level of the detected ambient signal. The system may compensate for this increase in the ambient light signal that is not correlated with a change in the sensor positioning, in part so that the gain change is distinguished from a change in sensor positioning. In a further example, the system may change the LED emitter brightness, resulting in a change in the detected light signal. The system may compensate for these changes in the detected signal amplitude to distinguish them from a change in the sensor positioning. It will be understood that the system may make any adjustments in gain, amplification, frequency, wavelength, amplitude, any other suitable adjustments, or any combination thereof. It will be understood that the adjustments may be made to the emitted photonic signal, the received signal, any signal following a number of processing steps, any other suitable signals, or any combination thereof.

In step 506, the system may process the received light signal to obtain a first signal. The first signal may correspond to detected ambient light signal. In some embodiments, the detected ambient light signal may, for example, correspond to detected ambient signal 222 of FIG. 2B. The first signal may be extracted from the received signal using, for example, demultiplexer 154 of FIG. 1. The processing of the light signal to obtain the first signal may be implemented using any suitable components of physiological monitoring system 100 of FIG. 1, physiological monitoring system 310 of FIG. 3, processing system 400 of FIG. 4, any other suitable components, or any combination thereof.

In step 508, the system may process the received light signal to obtain a second signal. In some embodiments, the second signal may correspond to the detected light signal, that is, the combination of the detected emitted photonic signal and the detected ambient light. In some embodiments, the second signal need not include the ambient light component. The second signal may correspond to one or more wavelengths of emitted light, for example, an IR signal, a red signal, any other suitable signal, or any combination thereof. The processing of the light signal to obtain the first signal may be implemented using any suitable components of physiological monitoring system 100 of FIG. 1, physiological monitoring system 310 of FIG. 3, processing system 400 of FIG. 4, any other suitable components, or any combination thereof.

In step 510, the system may analyze the first and second signals to identify similar behavior. For example, the analysis may include a comparison of the first signal (e.g., the detected ambient light) to the second signal (e.g., the detected light signal). Comparisons may include subtraction, division, multiplication, integration, any other suitable function, or any combination thereof. Comparisons may also include time-domain comparisons. Similar behavior may include, for example, signals at equal amplitudes, signals showing parallel changes, signals with the same or similar trends, signals with equal or similar slopes, signals changing in a non-linear but parallel trend, any other suitable similar behavior, or any combination thereof. For example, a detected ambient signal level may be compared to the moving average of the signal corresponding to the emitted photonic signal. In some embodiments, comparing multiple signals may help identify a sensor-off or other undesirable system condition from an external, unrelated change. For example, a large increase in ambient light caused by switching on an examination room light source may cause the ambient light signal to cross a threshold, but, for example, may not cause the same change in the detected emitted light signal. Thus, comparing the detected ambient signal to another signal may help classify an ambient signal change. In another example, an external detector, for example, on the monitor, may be used to determine an ambient light level that could be used to normalize changes in the detected ambient signal of the sensor.

The system may determine characteristics of the first signal, the second signal, any other suitable signal, or any combination thereof. Characteristics may include the signal level, amplitude, rate of change, slope, moving average, other trend, any other suitable characteristic, or any combination thereof. For example, a trend may include a first derivative of the amplitude signal. A characteristic may include a combination of parameters. For example, a trend may include the magnitude and polarity of the first derivative. In another example, the characteristic may include the signal amplitude and the polarity of the first derivative. Characteristics may be relative, absolute, or any combination thereof. For example, the signal level may be the absolute amplitude. In another example, the signal level may be relative to a baseline or to another signal. Determining the signal level may include any suitable processing equipment described above. The system may apply to the light signal filtering, smoothing, averaging, any other suitable technique, or any combination thereof. For example, the light signal may be filtered to remove noise. In another example, the signal may be smoothed or averaged to remove transient signals.

In some embodiments, the system may use complex and/or different comparisons of the two or more signals or characteristics of the signals. For example, the system may compare the difference of the slopes of two signals to a threshold or target value to determine parallel behavior. The system may compare derivatives, averages, integrals, slopes, trends, any other suitable operation, or any combination thereof. For example, the system may compare the first derivatives of two signals by subtracting one from the other. In place of subtraction, the system may also add, multiply, or divide. More complex data sets may include matrix cross products, matrix dot products, convolutions, other suitable operations, or any combination thereof. In some embodiments, signal processing may include wavelet transforms, scalograms, Fourier transforms, inverse Fourier transforms, other transforms, impulse response filters, any other suitable signal processing techniques, or any combination thereof.

In some embodiments, the system may include one or more target values or threshold levels related to the comparison of signals or signal characteristics. The thresholds may be used to identify similar behavior in multiple signals. A comparison metric reaching or crossing a threshold may result in an alarm being triggered, a flag being set, an indication being generated, a signal being generated, any other suitable output, or any combination thereof. For example, if the difference between two signals remains below 10 mV for 5 seconds, the behavior may be identified as similar. Thresholds may be predetermined, set by the user, determined based on historical information, determined based on characteristics related to the patient, determined based on characteristics of the sensor and system, determined based on any other suitable criteria, or any combination thereof. Thresholds may be constant or vary in time. The threshold may include multiple threshold values corresponding to multiple characteristics.

In some embodiments, the threshold may be set during a reset period. For example, the reset period may be triggered by a user to indicate a normal operating state of the system. The normal operating state may include proper positioning of the sensor. The reset mode may include setting a normal level or trend for the detected ambient signal and determining a threshold based on that level or trend. In some embodiments, a reset period may be triggered automatically based on time, sensor connections, signal conditions, a physiological condition or event, any other suitable triggers, or any combination thereof.

In step 512, the system may determine that the physiological sensor is not properly positioned. The system may determine this based on the analysis of step 510. For example, if a particular similar behavior or relationship is identified between the signals or signal characteristics, a probe-off condition may be identified. Similar behaviors may include mimicking-equal behavior, mimicking-parallel behavior, nonlinear scaling, any other suitable behavior, or any combination thereof. In some embodiments, a behavior based on a single characteristic (which may be derived from one or more signals) may be used to identify flatness, low signal level, high signal level, strong ambient behavior, any other suitable behavior, or any combination thereof. The system may identify the aforementioned behaviors as being indicative of a probe-off condition.

In some embodiments, the system may use multiple criteria to determine a probe-off condition. The multiple indicators may be combined using any suitable logic technique, algorithmic technique, polling technique, weighted technique, any other suitable technique, or any combination thereof. In some embodiments, a sequence of indicators may be included in determining a probe-off condition. In some embodiments, the system may determine a confidence value related to the possibility of a probe-off condition based on the criteria. In some embodiments, a confidence value is compared to a threshold to identify a probe-off condition.

In a subsequent step (not shown), the system may provide an indicator that the physiological sensor is not properly positioned. The indication may be based on any of the determinations that the sensor is improperly positioned as described herein. Indicators may include audible indications such as a voice alert, beep, or siren. Indicators additionally or alternatively may include visual indications such as lights, LEDs, computer screen readouts, mechanical flags, blinking or patterned use of any of the aforementioned, the use of particular colors, any other suitable visual indicator, or any combination thereof. Indicators may additionally or alternatively include communications such as communications sent to a cell phone, pager, text message, internet terminal, email, phone, fax, remote server, any other suitable communication, or any combination thereof. For example, a blinking red message may appear on a remote nurse's station computer in a hospital setting. In another example, a bedside monitor may emit a beeping sound when a probe-off condition is detected. In some embodiments, any or all of the aforementioned indicators may be graduated or otherwise altered based on a confidence that there is a probe-off condition, the duration of the probe-off condition, a sensitivity setting, any other suitable parameters, or any combination thereof.

Figure 7:
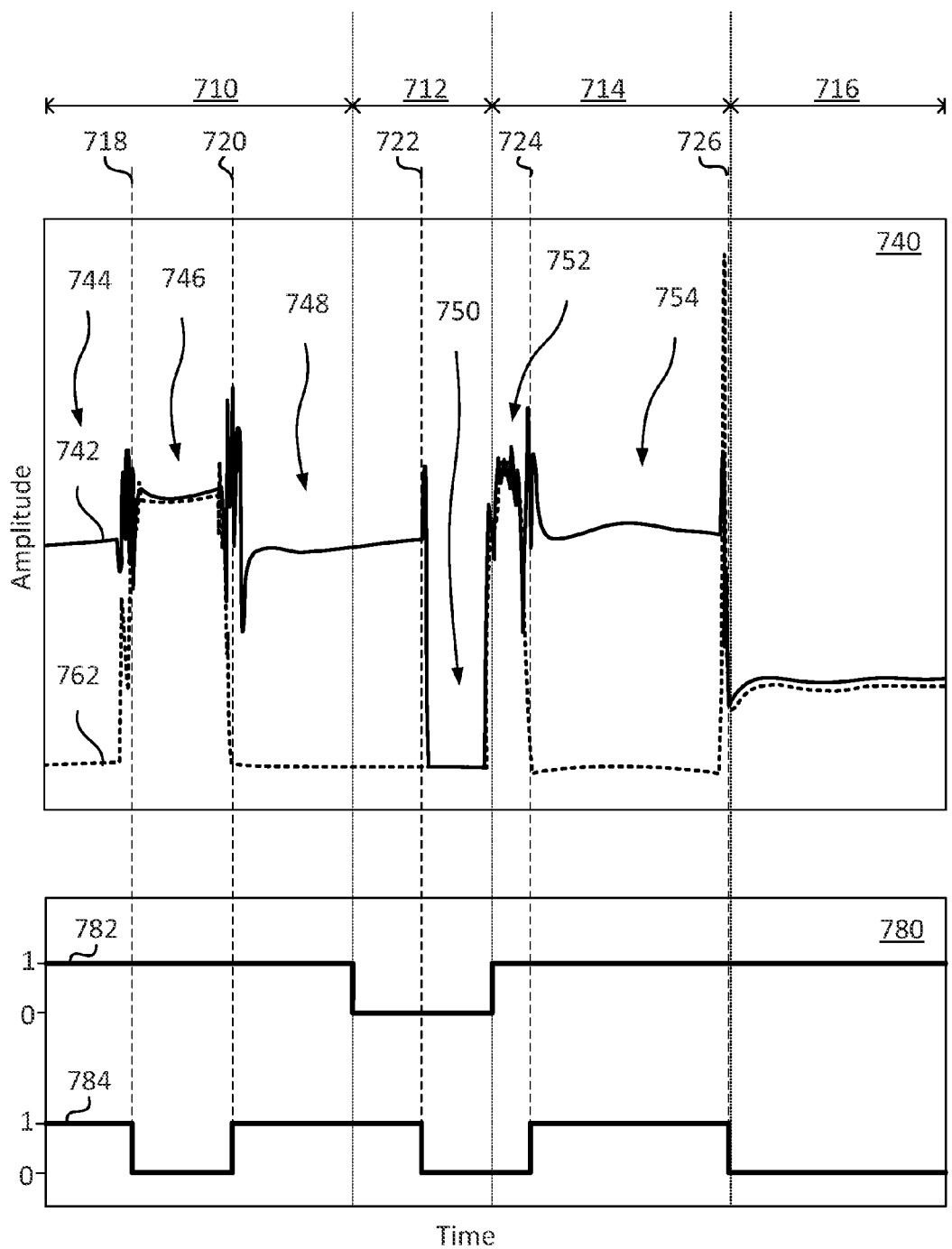
FIG. 7 shows further illustrative plots of physiological monitoring system signals in accordance with some embodiments of the present disclosure.
Figure 8:
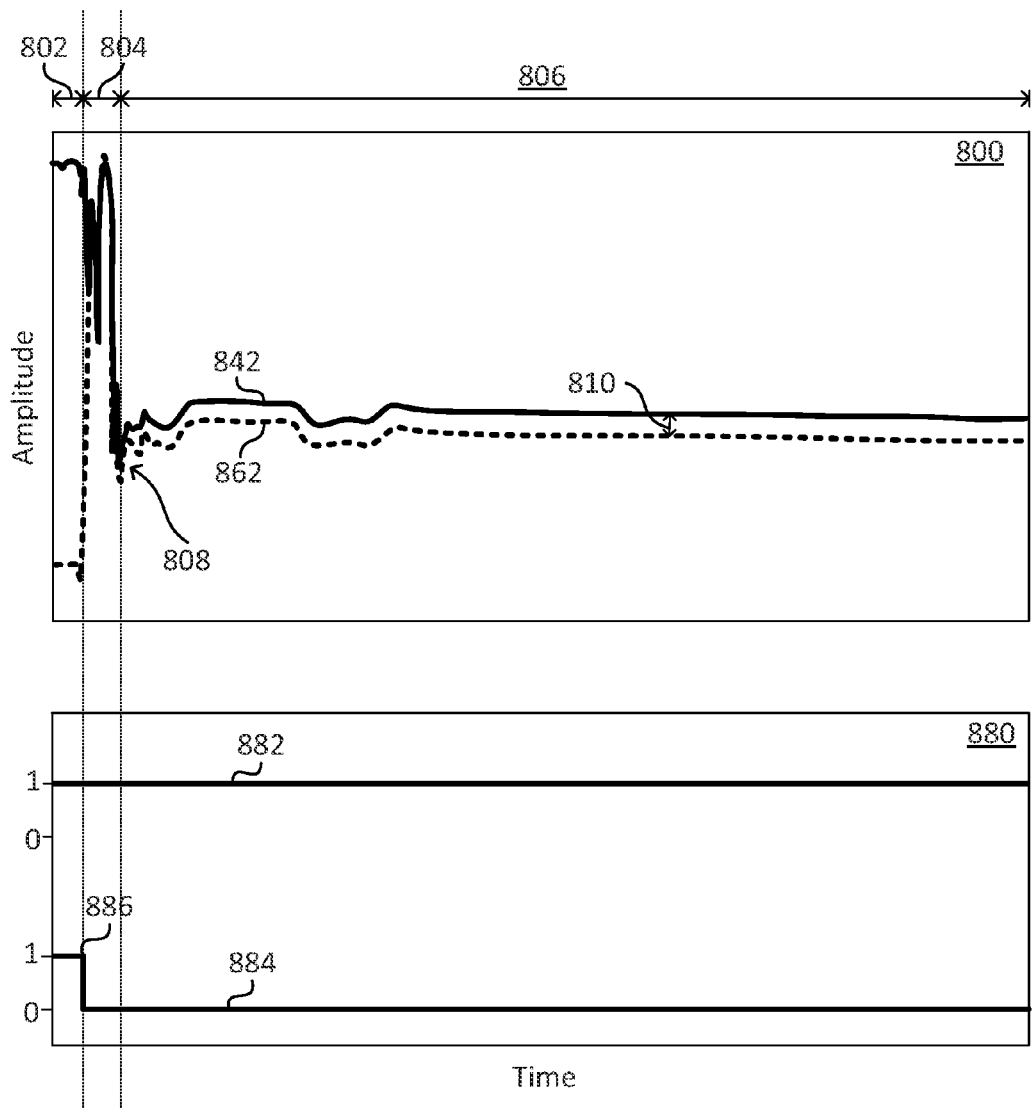
FIG. 8 shows a further illustrative plot of physiological monitoring system signals in accordance with some embodiments of the present disclosure.

It will be understood that the above described probe-off detection techniques are merely exemplary and that any suitable signal characteristics or combination of signal characteristics may be used with any suitable thresholds or combination of thresholds to determine a probe-off condition. The following FIGS. 6-8 show illustrative examples of detected ambient signals and detected light signals used to determine a probe-off condition.

Figure 6:
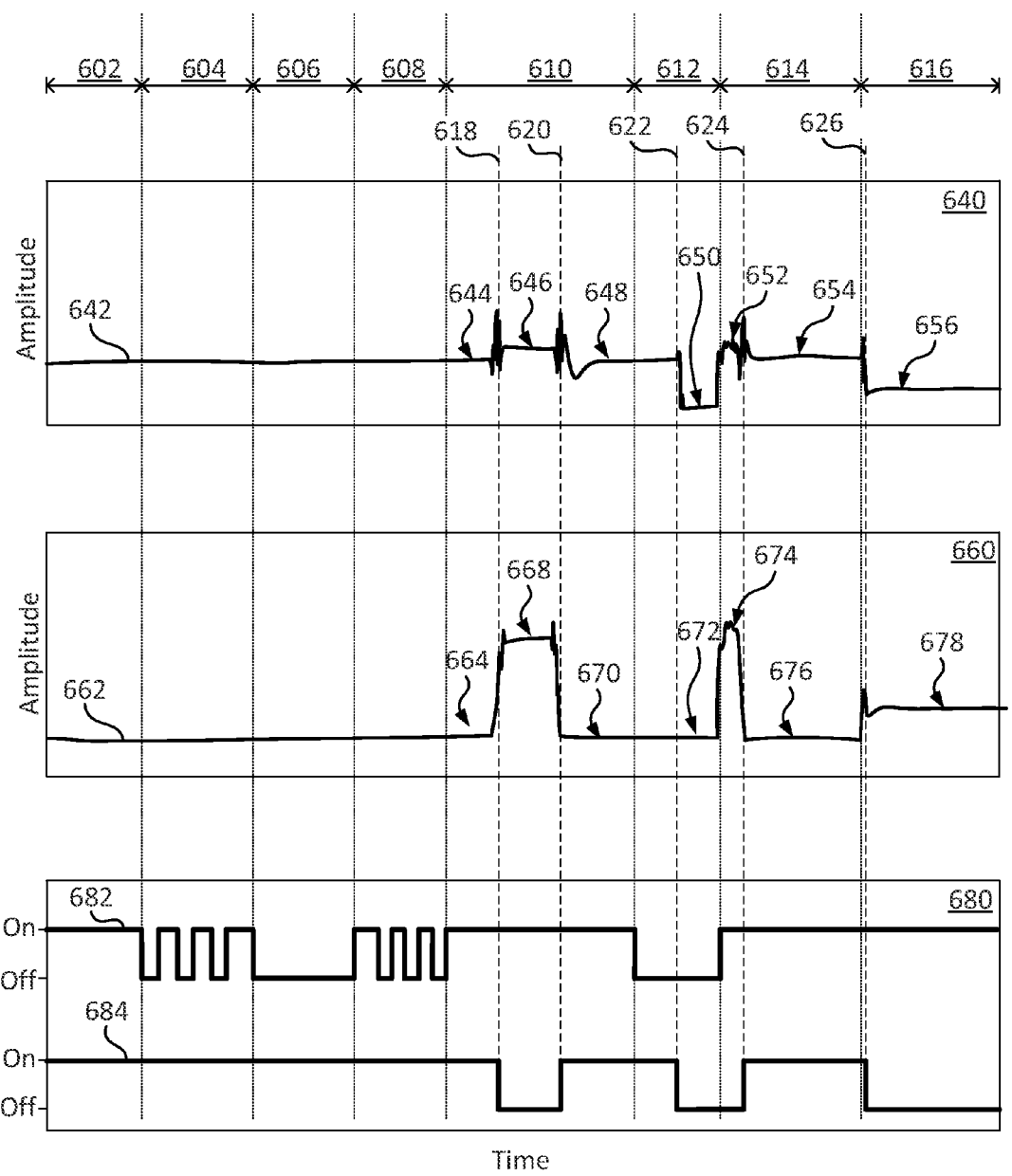
FIG. 6 shows illustrative plots of physiological monitoring system signals in accordance with some embodiments of the present disclosure.

FIG. 6 shows illustrative plots 640, 660, and 680 of physiological monitoring system signals in accordance with some embodiments of the present disclosure. Plot 640 may include information related to a detected light signal, such as the light signal detected during the IR "on" period of a multiplexed received light signal. Plot 660 may include information related to a detected ambient signal, such as the light signal detected during the "off" period of a multiplexed received light signal. Plot 680 may include information related to light levels and sensor positioning. The signals of plot 680 are indicative of manually controlled test conditions, and the signals of plots 640 and 660 include signals received under those test conditions. Plot 640, plot 660, and plot 680 may illustrate detected light signal and detected ambient signal levels received by the system when the ambient light level and sensor position are varied. The signals of plots 640 and 660 and elsewhere may have been filtered, processed, scaled, or otherwise modified such that typical pulse features are not illustrated in FIG. 6. For example, the periodic plethysmography waveforms may not be visible due to the horizontal and or vertical scale of the plots. In another example, the signals may be filtered by the system to remove these variations for the purposes of determining a probe-off condition. It will be understood that these signals and plots are merely exemplary and that any suitable signals and analysis may be used.

Plot 640, plot 660, and plot 680 have abscissa axes in units of time. In some embodiments, the axes may be on the same time scale. For example, the plots as illustrated may show approximately five minutes of signals. Plot 640 and plot 660 may have ordinate axes in units of amplitude. Plot 680 may have arbitrary ordinate axes.

Plot 640 may include detected light signal 642. Detected light signal 642 may include information related to an emitted photonic signal emitted by the system and detected ambient light. In some embodiments, detected light signal 642 need not include detected ambient light. Detected light signal 642 may have been processed by ambient subtractor 162 of FIG. 1, demultiplexer 154 of FIG. 1, pre-processor 420 of FIG. 4, any other suitable processing equipment, or any combination thereof. Detected light signal 642 may include information related to light detected during drive pulses of a drive pulse modulation, such as red drive pulse 202 or IR drive pulse 204 of FIG. 2A. For example, detected light signal 642 may include information related to the amplitude of the received IR signal. In some embodiments, some or all of the IR light emitted by the system may be attenuated, reflected, absorbed, or otherwise altered by interacting with the subject. In some embodiments, detected light signal 642 may include information related to the amplitude of the received red signal. In some embodiments, detected light signal 642 may include information related to any suitable light source, or any combination of light sources. In some embodiments, information from light sources may be combined to generated detected light signal 642 by averaging, summation, weighted summation, integration, any other suitable processing step, or any combination thereof. For example, information from a red and IR signal may be normalized and combined to generate detected light signal 642. In another example, a first light source may be weighted more heavily than a second light source in combining to form a combined detected light signal 642.

Plot 660 may include detected ambient signal 662. Detected ambient signal 662 may include information related to the amplitude of light received during an "off" or dark period of a drive pulse modulation. For example, detected ambient signal may include information related to light received during "off" period 220 of FIG. 2A, as processed by ambient subtractor 162 of FIG. 1, demultiplexer 154 of FIG. 1, any other suitable processing equipment, or any combination thereof.

In some embodiments, signal noise, ringing, and/or transients may occur at or near the point in time when a sensor is attached or removed from a subject. This can be seen, for example in detected light signal 642 at time point 618. The noise may be related to, for example, changes in signal processing, changes in front end amplification, increased amounts of reflected light when the sensor is partially out of proper position, any other suitable sources of noise, or any combination thereof. In some embodiments, this noise may be identified and ignored by the system in determining a probe-off condition.

The signals of FIG. 6 may, for example, be obtained from a forehead pulse oximeter sensor. Other suitable sensors may be used including, for example, a fingertip, earlobe, wrist, arm, foot, other suitable sensor, or any combination thereof. In some embodiments, different sensors may produce different signals, however it will be understood that the techniques described herein may be applied to multiple sensor types with appropriate modifications. For example, a sensor such as a fingertip sensor which may rely primarily on transmitted light rather than the reflected light of a forehead sensor may result in very high detected light signals being received when the sensor is improperly positioned in a dark room—rather than low signal levels. Thresholds, target values, time windows, other signal processing parameters, and any combination thereof may be adjusted based on the sensor and measurement type.

Plot 680 indicates manually controlled test conditions used to generate the above described detected signals. Plot 680 includes environmental light level signal 682. Environmental light level signal 682 may include information related to the amount of ambient light near the sensor. Changes in environmental light level signal 682 may be indicative of the test conditions changing. For example, the environmental light level signal 682 at signal level "On" may be indicative of the room lights where the system is located being on, while signal level "Off" may be indicative of the room lights being off. In some embodiments, the environmental light level signal 682 may be indicative of the control of room lighting, examination lights, heat sources, any other suitable sources of ambient light, or any combination thereof. It will be understood that the use of "On" and "Off" values for environmental light level signal 682 is merely exemplary and that light levels may vary continuously.

Plot 680 includes sensor positioning signal 684. Sensor positioning signal 684 may include information related to the proper or desired positioning of a sensor, as controlled during test conditions used in generating the signals of plots 640 and 660. For example, changes in the levels of sensor positioning signal 684 may be indicative of manual changes in the sensor position during test conditions used to generate the signals of plots 640 and 660. In some embodiments, sensor positioning signal 684 at signal level "On" may be indicative of the sensor being properly positioned. In some embodiments, sensor positioning signal 684 at signal level "Off" may be indicative of the sensor being improperly positioned. For example, an improperly positioned sensor may be a probe-off condition. It will be understood that the use of "Off" and "On" values for sensor positioning signal 684 is merely exemplary.

In time interval 602, the system may be under constant natural light conditions from a window with a properly attached forehead sensor. Accordingly, environmental light level signal 682 is "On" and sensor positing signal 684 is "On." The signal levels of time interval 602 may, for example, be indicative of signals received for 30 seconds.

In some embodiments, the behavior of detected light signal 642 and detected ambient signal 662 in time interval 602 may be indicative of a baseline behavior in the system. In time interval 602, environmental light level signal 682 remains constant and the sensor is properly positioned. As illustrated the signal levels of both detected light signal 642 and detected ambient signal 662 remain relatively constant. In some embodiments, this baseline behavior may be used to establish a baseline noise threshold, to establish alarm thresholds, to reset parameters, for any other suitable purpose, or any combination thereof.

In time interval 604, environmental light level signal 682 is varied and sensor positioning signal 684 is "On," indicative of the sensor being properly positioned. For example, the system may be operated in a room with the room lights switched off and a window shade rapidly opened and closed, while the sensor is properly positioned. The signal levels of time interval 604 may, for example, be indicative of signals received for 30 seconds.

In some embodiments, the behavior of detected light signal 642 and detected ambient signal 662 in time interval 604 may be indicative of an insensitivity to changing ambient light conditions when the sensor is properly positioned. In time interval 604, environmental light level signal 682 varies between "Off" and "On." As illustrated, the signal levels of both detected light signal 642 and detected ambient signal 662 remain relatively constant, despite this variation. In some cases, stronger ambient light may result in a change in the detected light levels. It is expected, however, that a properly positioned sensor will reduce the impact of varying ambient light conditions on detected signals. That is, when the sensor is properly positioned, changes in ambient light may have little effect on the detected light signal 642 and the detected ambient signal 662.

In time interval 606, environmental light level signal 682 is "Off." For example, the system may be operated in a dark room. In time interval 606, sensor positioning signal 684 is "On," indicative of the sensor being properly positioned. The signal levels of time interval 606 may, for example, be indicative of signals received for 30 seconds under dark conditions with a properly attached forehead sensor.

In some embodiments, the behavior of detected light signal 642 and detected ambient signal 662 in time interval 606 may be indicative of a baseline behavior in a dark room of the system. In time interval 606, environmental light level signal 682 remains "Off" and the sensor positioning signal remains at "On." As illustrated the signal levels of both detected light signal 642 and detected ambient signal 662 remain relatively constant. As illustrated, both the detected light signal 642 and detected ambient signal 662 are received at substantially the same amplitudes as in time interval 602 where the environmental light level was higher. This may be, for example, indicative of a properly positioned sensor's ability to exclude ambient light effects.

In time interval 608, environmental light level signal 682 is varied. For example, the system may be operated in a room with the room lights switched on and off. In time interval 608, sensor positioning signal 684 is "On," indicative of the sensor being properly positioned.

In some embodiments, the behavior of detected light signal 642 and detected ambient signal 662 in time interval 608 may be indicative of an insensitivity to changing environmental light conditions when the sensor is properly positioned. In some embodiments, the conditions in time interval 608 may be similar to those in time interval 604, except a level of electric light is varying as opposed to the amount of sunlight entering the room. As illustrated, the signal levels of both detected light signal 642 and detected ambient signal 662 remain relatively constant, despite the variations in environmental light. This may indicate that the sensor is properly positioned.

In time interval 610, environmental light level signal 682 may be "On." For example, the system may be operated in a room with the room lights switched on. In time interval 610, the sensor may be removed and reapplied. Sensor positioning signal 684 may be "On" during the beginning of time interval 610, "Off" between time point 618 and time point 620, and "On" following time point 620. For example, the sensor may have been removed at time point 618 and reapplied at time point 620.

In some embodiments, the behavior of detected light signal 642 and detected ambient signal 662 in time interval 610 may be indicative of the sensor being removed and reattached while operating in an illuminated room. In time interval 610, the sensor (e.g., a forehead sensor) may be removed from the patient at time point 618. The level of detected light signal 642 may increase from a relatively lower level in region 644 to a relatively higher level in region 646 substantially coincident with the removal of the sensor at time point 618. The level of detected ambient signal 662 may increase from a relatively lower level in region 664 to a relatively higher level in region 668 substantially coincident with the removal of the sensor at time point 618. The increase in both detected light signal 642 and detected ambient signal 662 may be indicative of an increased amount of light reaching the detector. In some embodiments, shielding or light blocking structures may have prevented ambient light from reaching the detector while it was properly positioned, but not while it is removed from the subject. In some embodiments, the changes in signal levels may be in part attributed to increased ambient light reaching the detector, light from the emitters that is not attenuated as much as it would have been in a properly positioned sensor arrangement reaching the detector, sensor noise, other suitable signal sources, or any combination thereof.

At time point 620, the sensor may be reattached, as indicated by sensor positioning signal 684 changing from "Off" to "On." As illustrated, detected light signal 642 in region 648 following time point 620 may return to substantially the same level as region 644. Detected ambient signal 662 in region 670 may return to substantially the same level as region 664. This may, for example, be indicative of the stability of the system and show that the changes in the signal levels are primarily related to changes in sensor positioning.

In some embodiments, the similar behavior of both detected light signal 642 and detected ambient signal 662 in region 646 and region 668, respectively, may be recognized by the system as a probe-off condition. Considering an increase in both signals at the same time may be advantageous over considering an increase in only the detected ambient signal or only the detected light signal. In some embodiments, the increase may be recognized by comparing one or both signal levels to a threshold. In some embodiments, signal levels, trends, slopes, derivatives, behaviors, other related signals, or combinations thereof may be compared to a threshold, target value, other suitable criteria, or any combination thereof. For example, both the ambient and the detected light signal crossing a threshold at substantially the same time may be recognized by the system as a probe-off condition.

In time interval 612, environmental light level signal 682 may be "Off." For example, the system may be operated in a dark room. In time interval 612, the sensor may be removed at time point 622, as indicated by the change in sensor positioning signal 684 at time point 622 from "On" to "Off."

In some embodiments, the behavior of detected light signal 642 and detected ambient signal 662 in time interval 612 may be indicative of the sensor being removed while operating in a dark room. In time interval 612, the sensor (e.g., a forehead sensor) may be removed from the patient at time point 622. The level of detected light signal 642 may decrease to a relatively lower level in region 650 substantially coincident with the removal of the sensor at time point 622. The level of detected ambient signal 662 may remain relatively constant in region 672 substantially coincident with the removal of the sensor at time point 622. The decrease in detected light signal 642 coincident with the constant level of detected ambient signal 662 may be indicative of less light from the emitters reaching the detector. In a reflective arrangement such as a forehead sensor, this would be expected when the sensor is removed because it relies on a reflective structure for light to be communicated from the emitters to the detectors. The relatively constant level of detected ambient signal 662 in time interval 612 may be indicative of a relatively constant amount of light reaching the detector when the environmental light level signal 682 is at "Off."

In time interval 614, the system may be operated in a room with the room lights switched on and the sensor reattached at time point 624. The environmental light level signal 682 is "On." At time point 624, sensor positioning signal 684 may change from "Off" to "On."

For example, the behavior of detected light signal 642 and detected ambient signal 662 in time interval 614 may be indicative of a light source being switched on followed by a sensor being reattached to a patient. The level of detected light signal 642 may increase from the relatively lower level in region 650 to a relatively higher level in region 652 substantially coincident with the increase in environmental light. The level of detected light signal 642 may decrease in region 654 substantially coincident with the reattachment of the sensor at time point 624. The level of detected ambient signal 662 may increase from the relatively lower level in region 672 to a relatively higher level in region 674 substantially coincident with the increase in environmental light. The level of detected ambient signal 662 may decrease in region 676 substantially coincident with the reattachment of the sensor at time point 624.

In some embodiments, the behavior in time intervals 612 and 614 may illustrate the benefit of using a comparison of detected light signal 642 and detected ambient signal 662, rather than a single signal, to detect a probe-off condition. For example, there is no significant change in detected ambient signal 662 at time point 622, due to the dark room, despite the sensor being removed as indicated by sensor positioning signal 684. Using only detected ambient signal 662 would result in a false-negative, since the probe-off condition would not be determined. However, the probe-off condition at time point 622 can be determined by also using the detected light signal 642. By monitoring both detected light signal 642 and detected ambient signal 662, the system may detect conditions such as mimicking-equal, mimicking-parallel, or non-linear scaling behavior, as described above. The system may identify these behaviors as being indicative of a probe-off condition.

It will be understood that the system may identify the change using any suitable signal levels, trends, or any combination thereof, along with any suitable thresholds, targets, other suitable criteria, or any combination thereof. Any suitable polling, averaging, index values, or other suitable combination of multiple criteria or tests may be used. For example, the system may require a particular number of threshold crossings among one or more signals to indicate a probe-off condition.

In time interval 616, the system may be operated in a room with the room lights switched on while the sensor is removed from the subject and, for example, placed on a surface with the detector receiving light both from the emitters and from environmental sources. In this position, the system receives the same amount of ambient light during both the "on" and "off" periods of the emitted photonic signal, and receives a constant emitted photonic signal component during the "on" period due to light from the emitters reaching the detector directly. Accordingly, there is a parallel, offset behavior between detected light signal 642 and detected ambient signal 662 that will be shown in further detail below in time interval 740 of FIG. 7. The environmental light level signal 682 remains "On" in time interval 616, and the sensor positioning signal 684 changes from "On" to "Off" at time point 626.

In some embodiments, the behavior of detected light signal 642 and detected ambient signal 662 in time interval 616 may be indicative of signal behavior when a forehead sensor is positioned away from a subject in the presence of ambient light. At time point 626, the sensor may be removed from the subject. In region 656, detected light signal 642 may decrease to a relatively lower level as compared to the level before time point 626. This may be indicative of a decreased amount of light reaching the detector due to the lack emitted light reflected by a patient, yet some emitted light may still reach the detector due to diffusion and reflection from other surfaces. In region 678, detected ambient signal 662 may increase to a relatively higher level as compared to the level before time point 626 due to increased ambient light reaching the now-exposed detector. The system may recognize elements of this behavior as relating to a probe-off condition, as will be described in further detail below.

FIG. 7 shows illustrative plots 740 and 780 of physiological monitoring system signals in accordance with some embodiments of the present disclosure. The plots of FIG. 7 may include information from the plots of FIG. 6 shown in more detail. Plot 740 may include information from time intervals 610, 612, 614 and 616 of both plot 640 and plot 660 of FIG. 6. For example, time intervals 710, 712, 714, and 716 may relate to time intervals 610, 612, 614 and 616 of FIG. 6, respectively. Similarly, time points 718, 720, 722, 724, and 726 may relate to time points 618, 620, 622, 624, and 626 of FIG. 6, respectively.

Plot 740 and plot 780 have abscissa axes in units of time. In some embodiments, the axes may be on the same time scale. For example, the plots as illustrated may show approximately three minutes of signals. Plot 740 may have ordinate axes in units of amplitude. As illustrated, plot 740 may include information from both plot 640 and plot 660 of FIG. 6 on a shared ordinate axis. Plot 780 may have arbitrary ordinate axes.

Plot 740 may include detected light signal 742 and ambient light signal 762. The amplitude of the detected light signal 742 and ambient light signal 762 may be indicative of the amount of light detected by a detector during an "On" period and "Off" period, respectively, of a light drive modulation. The amplitude of the detected light signal 742 may include an IR, red, other suitable light signal, or any combination thereof. As depicted, detected light signal 742 also includes ambient light.

Characteristics of plot 740 may relate to the characteristics described for plots 640 and 660 of FIG. 6. Plot 780 may include light level signal 782 and sensor positioning signal 784. Characteristics of plot 780 may relate to the characteristics indicated by plot 680 of FIG. 6. The signals may be obtained and processed as described above for the signals illustrated in the plots of FIG. 6.

In time interval 710, the sensor may be removed at time point 718 and reattached at time point 720, as indicated by sensor positioning signal 784. The sensor may be operating in an illuminated environment, as indicated by environmental light level signal 782. In region 744, the level of detected light signal 742 may be relatively higher than the level of detected ambient signal 762 because, for example, the sensor is properly positioned and some or all of the ambient light is blocked from reaching the detector by the sensor body. In region 746 following time point 718 where the sensor is removed from the subject and directly exposed to environmental light, detected light signal 742 and detected ambient signal 762 may go to a relatively higher, common level. This common movement may be referred to as mimicking-equal behavior, and may be recognized as being indicative of a probe-off condition. The behavior may be identified, for example, by subtracting detected light signal 742 from ambient detected light signal 762 and generating a substantially zero amplitude signal within a time window. A certain amount of deviation from zero may be permitted in identifying the mimicking-equal behavior. Deviations may arise from line noise, equipment noise, any other source, or any combination thereof. In some embodiments, the signals in region 746 may be indicative of mimicking-parallel behavior. Following time point 720, where the sensor is reattached as indicated by sensor positioning signal 784, the levels of both detected light signal 742 and detected ambient signal 762 return to levels similar to those in region 744 prior to time point 718. In some embodiments, this behavior may not be recognized if only changes in detected light signal 742 were analyzed to detect a probe-off condition. The movement of both signals to a common, higher level with common movement indicates that both the detected emitted signal and the detected ambient signal are comprised substantially of environmental light. For example, the sensor receiving no, or a small amount of, light corresponding to the emitted photonic signals. The system may identify this behavior as indicating that the sensor is not properly positioned on the patient.

In time interval 712, the sensor may be operating in a dark environment, as indicated by environmental light level signal 782. At time point 722, the sensor may be removed from the subject. In region 748, the level of detected light signal 742 may be relatively higher than the level of detected ambient signal 762 due to the reflected emitted light reaching the detector and the lack of environmental light. In region 750 following time point 722, where the sensor is removed from the subject, the level of detected light signal 742 may drop to a level similar to the level of detected ambient signal 762. The level of detected ambient signal 762 may remain relatively unchanged, due to the lack of environmental light. This similarity between detected light signal 742 and detected ambient signal 762 in region 750, sometimes referred to as mimicking-equal, or following behavior, may be recognized as a probe-off condition. In some embodiments, mimicking-equal in combination with a low detected light signal amplitude may further be recognized as being indicative of a probe-off condition.

In time interval 714, the sensor may operate in an illuminated environment, as indicated by environmental light level signal 782. The sensor may be removed from the patient during region 752 of time interval 714, reattached at time point 724, and remain attached during region 754. In region 752, where the sensor is operating removed from the subject in an illuminated room, changes in detected light signal 742 and detected ambient signal 762 may parallel each other. In some embodiments, the system may identify this behavior as being indicative of a probe-off condition, as described above. In some embodiments, region 752 may display a relatively higher amount of signal noise than, for example, region 750. In some embodiments, signal noise may be related to an improperly positioned sensor being moved in relation to ambient light sources, to cable connector noise, to other sources of noise, or any combination thereof. In some embodiments, the system may identify the increased noise as being indicative of a probe-off condition. In region 754 after time point 724, where the sensor is reattached as indicated by sensor positioning signal 784, detected light signal 742 and detected ambient signal 762 may return to varying independently.

In time interval 716, the sensor may be removed from the patient and placed, for example, on a table. The detector may be oriented such that it receives environmental light and a small amount of the emitted photonic signal, for example, by reflection from a surface. The sensor may be removed from the subject at time point 726 coinciding with the start of time interval 716. Behavior in time interval 716 may be indicative of a probe-off condition and will be discussed in detail in relation to FIG. 8 below. In some embodiments, a small offset may be present between detected light signal 742 and detected ambient signal 762. The offset may be, for example, due to the presence of some reflected emitted light, in contrast to the common movement of region 746 where none of the emitted photonic signal reaches the detector. The behavior may be referred to as mimicking-parallel and will be shown in detail in FIG. 8 below.

FIG. 8 shows illustrative plot 800 of physiological monitoring system signals in accordance with some embodiments of the present disclosure. FIG. 8 may include information from the plots of FIG. 6 and FIG. 7 shown in more detail. Plot 800 may include information from time interval 616 of both plot 640 and plot 660 of FIG. 6. Plot 800 may include information from time interval 716 of FIG. 7 in more detail.

Plot 800 may include detected light signal 842 and ambient light signal 862. The amplitude of the detected light signal 842 and detected ambient signal 862 may be indicative of the amount of light detected by a detector during an "On" period and "Off" period, respectively, of a light drive modulation. The amplitude of the detected light signal 842 may include an IR, red, other suitable light signal, or any combination thereof. As depicted, detected light signal 842 also includes ambient light.

Characteristics of plot 800 may relate to the characteristics described for plots 640 and 660 of FIG. 6. Plot 880 may include light level signal 882 and sensor positioning signal 884. Characteristics of plot 880 may relate to the characteristics indicated by plot 680 of FIG. 6.

The signals in plot 800 may include information from a sensor operating in an illuminated room, as indicated by environmental light level signal 882. The sensor, for example a forehead sensor, may be attached in time interval 802 and removed at a particular time, as indicated by time point 886 of sensor positioning signal 884. Upon removal of the sensor, it may be seen in time interval 804 that detected ambient signal 862 and detected light signal 842 vary together with a small, parallel offset. In the time immediately following removal of the sensor, there may be an increased amount of noise present in both signals. The system may recognize this increased amount of noise as being indicative of a probe-off condition. Additionally, the mimicking-equal behavior of time interval 804 which may correspond to an equal or approximately equal amount of light reaching the detector during both detected light signal and detected ambient signal periods, may be recognized by the system as being indicative of a probe-off condition.

In some embodiments, the mimicking-parallel behavior of the signals in region 806 may be indicative of a situation where the probe is removed and placed on or near a moderately reflective surface at time point 808. In an example, the emitter and detector may be facing the surface such that some of the emitted light reaches the detector and the sensor body blocks a portion of the ambient light from reaching the sensor. Offset 810 may be indicative of a particular amount of light from the emitters reaching the detector during the drive pulse cycle. Since this light is interacting with a constant, unchanging surface (as compared to subject tissue), the amount of reflected light is constant. Thus, the variations in the signals are attributed to variations in the ambient light, and the offset is attributed to the emitters. This relatively small offset with parallel signal behavior may be recognized by the system as being indicative of a probe off situation.

In some embodiments, offset 810 may be determined by subtracting detected ambient signal 862 from detected light signal 842. This subtraction would, for the illustrated signals, result in a small, relatively constant signal. This signal, or variations in the signal, may be compared to a threshold or target value to identify a probe-off condition. A threshold may be defined at a predetermined value, by user input, by historical information, by information related to the equipment, by any other suitable criteria, or any combination thereof. For example, the threshold may allow parallel behavior to be recognized within a tolerance level, such that signals that display a certain degree of parallel behavior are identified as indicating a probe-off condition. Variations in the offset or any other signal may be analyzed using, for example, slope, fractal dimension, any other suitable technique, or any combination thereof. In some embodiments, the system may use more complex mathematical comparisons of the two or more signals, as described above.

In some embodiments, offset parallel behavior may be observed by the system due to non-linear system response or processing. For example, sensor signal amplitude may be greater with respect to the number of incident photons at low light levels as compared to high light levels due to detector saturation. Offsets and non-linearity may also occur as a result of front end gain, filters, emitter spectrum variations, ambient light spectrum variations, other suitable sources of variations, or any combination thereof.

Non-linearity in the system may result in similar behavior between two signals where a relative change is apparent between the two signals. For example, where a detected ambient signal level increases by 100 mV then decreases by 200 mV, the detected light level may signal may increase 50 mV and then decrease by 100 mV. In some embodiments, the system may remove non-linearity by suitable processing steps, may detect probe-off conditions in the presence of non-linear comparisons by, for example, comparing the slopes of signals, may consider non-linearity by any other suitable technique, or any combination thereof.

Figure 9:
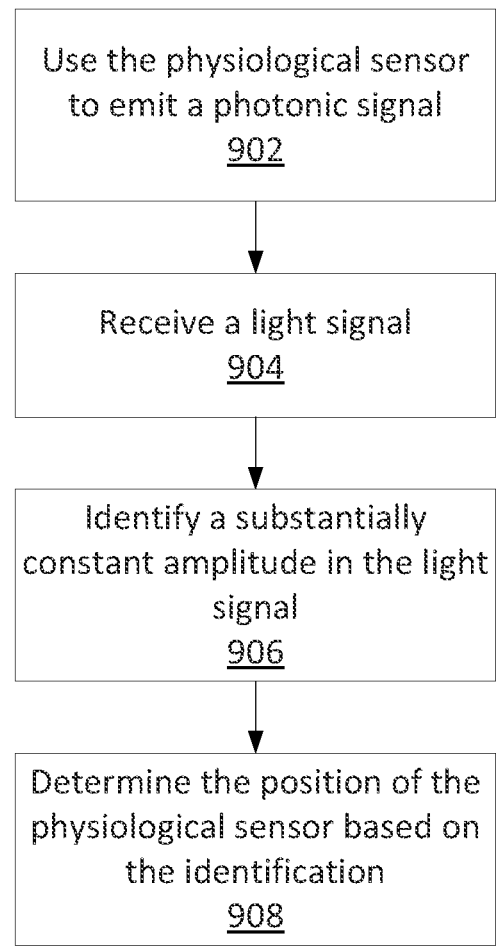
FIG. 9 is a flow diagram showing illustrative steps for determining a probe-off condition in accordance with some embodiments of the present disclosure.

FIG. 9 is flow diagram 900 showing illustrative steps for determining a probe-off condition in accordance with some embodiments of the present disclosure.

In step 902, the system may use the physiological sensor to emit a photonic signal. The system may emit a photonic signal including one wavelength of light, multiple wavelengths of light, a broad spectrum light (e.g., white light), or any combination thereof. For example, the photonic signal may include light from a red LED and light from an IR LED. The emitted photonic signal may be emitted, for example, by light source 130 of FIG. 1. In some embodiments, the emitted photonic signal may include a light drive modulation. For example, where the photonic signal includes a red light source and an IR light source, the light drive modulation may include a red drive pulse followed by an "off" period followed by an IR drive pulse followed by an off period. It will be understood that this drive cycle modulation is merely exemplary and that any suitable drive cycle modulation or combination of modulations may be used. In some embodiments, the photonic signal may include a cardiac cycle modulation, where the brightness, duty cycle, or other parameters of one or more emitters are varied at a rate substantially related to the cardiac cycle.

In step 904, the system may receive a light signal. The received light signal may include light from drive pulses or other emitted light in the emitted photonic signal that has interacted with the subject. The received light signal may be detected by, for example, detector 140 of FIG. 1. In some embodiments, a portion of the emitted light may be partially attenuated by the tissue of the subject before being received as a received light signal. In some embodiments, the received light may have been primarily reflected by the subject. For example, reflected light may be detected by a forehead-attached system where the emitter and detector are on the same side of the subject. In some embodiments, the received light may have been transmitted through the subject. For example, transmitted light may be detected in a fingertip-attached or earlobe-attached sensor.

In some embodiments, the received light signal may include an ambient light signal component and a component related to the emitted photonic signal. As described above, the system may determine a detected ambient signal, any other suitable signals, or any combination thereof.

In some embodiments, the detected ambient signal may, for example, include ambient signal 222 of FIG. 2B. In some embodiments, the system may subtract ambient signal 222 or a signal derived from ambient signal 222 from the received signal to generate an adjusted signal. The adjusted signal may be used to determine physiological parameters. In some embodiments, the system may determine an ambient signal for probe-off analysis before generating the adjusted signal. Separation of the ambient signal from the received signal may include, for example, demultiplexer 154 of FIG. 1, any other suitable equipment, or any combination thereof. Signal processing of the ambient component and emitted light component may include any suitable components of physiological monitoring system 100 of FIG. 1, physiological monitoring system 310 of FIG. 3, signal processing system 400 of FIG. 4, any other suitable components, or any combination thereof.

In some embodiments, the system may adjust or compensate a signal depending in part on the LED drive signal, the detector gain, other suitable system parameters, or any combination thereof. For example, increasing the gain on a detected signal may result in an increased ambient signal. The system may compensate for this increased ambient that is not correlated with a change in the sensor positioning. In a further example, the system may change the LED emitter brightness, resulting in a change in the detected signals. The system may compensate for these changes in the detected signal amplitude to distinguish them from a change in the sensor positioning. It will be understood that the system may make any adjustments in gain, amplification, frequency, wavelength, amplitude, any other suitable adjustments, or any combination thereof. It will be understood that the adjustments may be made to the emitted photonic signal, the received signal, a signal following a number of processing steps, any other suitable signals, or any combination thereof.

In step 906, the system may identify a substantially constant amplitude in the light signal. This behavior may be referred to as flatness. The light signal may include, as described above, a drive pulse light signal, an ambient light signal, any suitable processed signal, or any combination thereof. A substantially constant amplitude may be identified by a flatness value determined by comparing the signal to a target value, by analyzing a derivative of the signal, by determining a statistical parameter, determining a slope, determining a fractal or other dimension, by any other suitable technique, or any combination thereof. In some embodiments, a flatness value is compared to a threshold. For example, a moving average of a first derivative substantially close to zero may be recognized as a substantially constant amplitude. In another example, a slope between two particular threshold amounts may be recognized as a substantially constant amplitude. Characteristics and parameters may be considered, for example, within a fixed or moving time window. Statistical parameters may include means, standard deviations, variances, averages, filtered values, trends, any other suitable parameters, or any combination thereof. In some embodiments, a target value or other characteristic evaluation parameter may be based on system parameters, physiological characteristics, historical information, user input, any other suitable parameters, or any combination thereof. For example, a certain configuration of probe elements may be known to generate a particular signal level under standard ambient light levels when detached from a subject. In some embodiments, a signal level may be compared to a target or threshold by any suitable technique. For example, a signal level may be subtracted from a target level to identify a substantially constant amplitude.

In step 908, the system may determine the position of the physiological sensor based in part on the identification of the constant amplitude. For example, the system may determine a probe-off condition when a substantially constant amplitude is identified in one or more received light signals, or based on a combination of signals. For example, the system may determine the presence of a substantially constant amplitude in a detected light signal, an ambient light signal, any other suitable signal, or any combination thereof, and that constant amplitude may be recognized by the system as being indicative of a probe-off condition. It will be understood that a substantially constant amplitude alone may not necessarily indicate a probe-off condition. For example, flatness of the detected ambient signal may be a normal condition. In some embodiments, the system may consider a flatness in the detected light signal to be indicative of a probe-off condition. In some embodiments, the system may consider both the detected ambient signal and the detected light signal in determining a probe-off condition. For example, the system may consider a substantially constant amplitude of the detected light signal in combination with a high level of the detected ambient signal to be indicative of a probe-off condition, for example, as shown in region 806 of FIG. 8. In some embodiments, the constant amplitude may be related to a maximum detector input voltage or current. For example, an analog to digital converter (or other front end processing circuitry) may receive the maximum value it can process when a probe-off condition occurs in a fingertip sensor. In some embodiments, a substantially constant amplitude may be related to a minimum detector input, for example, when the light signal amplitude is substantially close to zero.

In an optional step (not shown), an indication of a probe-off condition may be provided as described above in relation to flow diagram 500 of FIG. 5.

Figure 10:
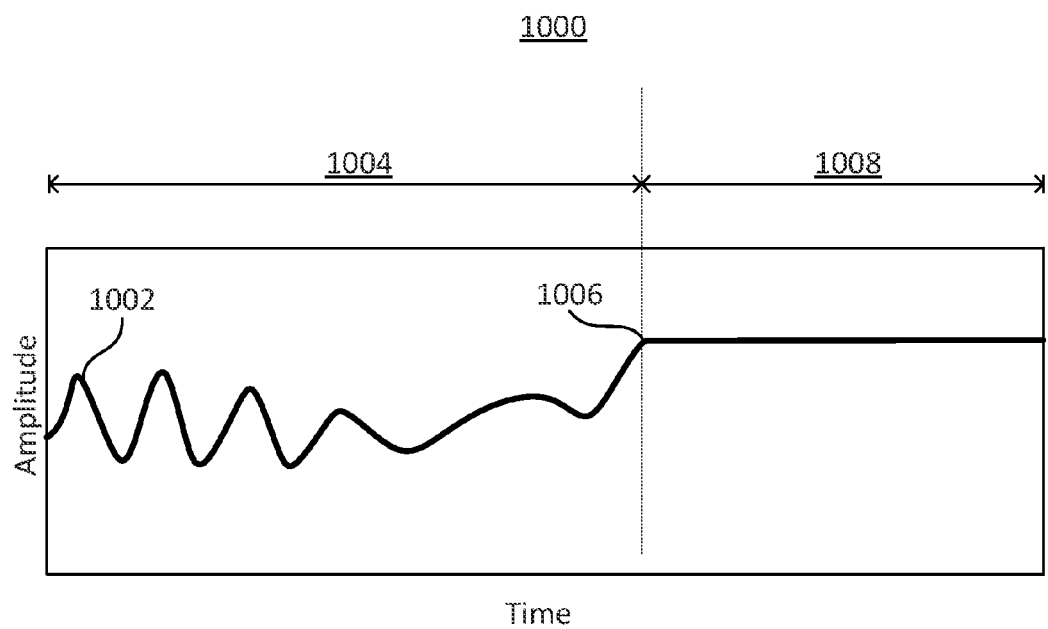
FIG. 10 shows an illustrative plot of a physiological monitoring system signal in accordance with some embodiments of the present disclosure.

FIG. 10 shows illustrative plot 1000 of a physiological monitoring system signal in accordance with some embodiments of the present disclosure. Signal 1002 may include any suitable system signal. For example, signal 1002 may include a detected light signal, an ambient light signal, a combination of detected light signals, any other suitable signals, or any combination thereof. In some embodiments, signal 1002 may be the signal received in step 904 of FIG. 9. In time interval 1004, a sensor of the system may be properly positioned and the system may be operating normally. The signal may show variations in amplitude related to physiological and/or system parameters. In time interval 1008 following time point 1006, signal 1002 may display a substantially constant amplitude. Time point 1006 may be related to a point where the system enters a probe-off condition. The system may identify the substantially constant amplitude or flatness of signal 1002 in time interval 1008. For example, the system may identify the substantially constant amplitude using the techniques described in step 906 of FIG. 9. The system may identify this probe-off condition based on the substantially constant amplitude of signal 1002 in time interval 1008 using the techniques described in step 908 of FIG. 9.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed:

1. A method for determining whether a physiological sensor is properly positioned on a subject, the method comprising:
    receiving a light signal using the physiological sensor;
    processing, using processing equipment, the light signal to obtain a first signal corresponding to ambient light;
    processing, using the processing equipment, the light signal to obtain a second signal corresponding to an emitted photonic signal and ambient light;
    analyzing, using the processing equipment, the first signal and the second signal to identify similar signal amplitude behavior; and
    determining, using the processing equipment, that the physiological sensor is not properly positioned based on the analysis.

2. The method of claim 1, wherein the physiological sensor comprises a pulse oximeter.

3. The method of claim 1, wherein receiving the light signal comprises receiving light from a first light emitting diode configured to emit a first wavelength of light and from a second light emitting diode configured to emit a second wavelength of light.

4. The method of claim 1, wherein the light signal is detected by a photoelectric detector.

5. The method of claim 1, wherein analyzing the first signal and the second signal to identify similar signal amplitude behavior comprises determining whether a difference in amplitudes of the first and second signals is substantially constant.

6. The method of claim 1, wherein analyzing the first signal and the second signal to identify similar signal amplitude behavior comprises determining whether a difference in slopes of the first and second signals is substantially constant.

7. The method of claim 1, wherein analyzing the first signal and the second signal to identify similar signal amplitude behavior comprises compensating for nonlinearity.

8. The method of claim 1, wherein analyzing the first signal and the second signal to identify similar signal amplitude behavior comprises:
    determining a value based on the first signal and the second signal; and
    comparing the value to a threshold.

9. The method of claim 8, wherein the value is selected from the group consisting of difference between the first and second signal, a flatness value, a confidence value, a slope value, an amplitude value, and combinations thereof.

10. The method of claim 1, wherein analyzing the first signal and the second signal to identify similar signal amplitude behavior comprises identifying a substantially constant amplitude in at least one of the first signal and the second signal.

11. The method of claim 1, wherein analyzing the first signal and the second signal to identify similar signal amplitude behavior comprises identifying a threshold crossing by both signals at substantially the same time.

12. The method of claim 1, wherein analyzing the first signal and the second signal to identify similar signal amplitude behavior comprises identifying at least one of a mimicking-equal behavior, a mimicking-parallel behavior, or a nonlinear scaling behavior of the first and second signals.

13. The method of claim 1, further comprising providing an indicator that the physiological sensor is not properly positioned.

14. The method of claim 1, further comprising compensating the received light signal for a light drive setting.

15. A system for determining whether a physiological sensor is properly positioned on a subject, the system comprising:
processing equipment configured to:
receive a light signal from the physiological sensor;
process the light signal to obtain a first signal corresponding to ambient light;
process the light signal to obtain a second signal corresponding to an emitted photonic signal and ambient light;
analyze the first signal and the second signal to identify similar signal amplitude behavior; and
determine that the physiological sensor is not properly positioned based on the analysis.

16. The system of claim 15, wherein the processing equipment comprises a pulse oximeter.

17. The system of claim 15, wherein the processing equipment is further configured to determine whether a difference in amplitudes of the first and second signals is substantially constant.

18. The system of claim 15, wherein the processing equipment is further configured to determine whether a difference in slopes of the first and second signals is substantially constant.

19. The system of claim 15, wherein the processing equipment is further configured to:
determine a value based on the first signal and the second signal; and
compare the value to a threshold.

20. The system of claim 15, wherein the processing equipment is further configured to identify a substantially constant amplitude in at least one of the first signal and the second signal.

21. The system of claim 15, wherein the processing equipment is further configured to provide an indicator that the physiological sensor is not properly positioned.

22. The system of claim 15, wherein the processing equipment configured to analyze the first signal and the second signal to identify similar signal amplitude behavior comprises processing equipment configured to identify at least one of a mimicking-equal behavior, a mimicking-parallel behavior, or a nonlinear scaling behavior of the first and second signals.

23. The method of claim 1, wherein the ambient light corresponds to light received from light sources other than light sources coupled to the physiological sensor.

24. The system of claim 15, wherein the ambient light corresponds to light received from light sources other than light sources coupled to the physiological sensor.

* * * * *